(12) United States Patent
Knopp et al.

(10) Patent No.: US 7,771,195 B2
(45) Date of Patent: ***Aug. 10, 2010

(54) POLAR ATTACHMENT DEVICES AND METHOD FOR A DENTAL APPLIANCE

(75) Inventors: Peter Knopp, Palo Alto, CA (US); Loc X. Phan, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 1313 days.

This patent is subject to a terminal disclaimer.

(21) Appl. No.: 10/863,991

(22) Filed: Jun. 9, 2004

(65) Prior Publication Data

US 2004/0229183 A1 Nov. 18, 2004

Related U.S. Application Data

(63) Continuation-in-part of application No. 10/632,482, filed on Aug. 1, 2003, now Pat. No. 7,059,850, which is a continuation-in-part of application No. 10/040,269, filed on Oct. 29, 2001, now Pat. No. 6,705,863.

(51) Int. Cl.
    *A61C 3/00* (2006.01)
(52) U.S. Cl. ............................................. 433/6; 433/24
(58) Field of Classification Search ................. 433/213, 433/6, 24
    See application file for complete search history.

(56) References Cited

U.S. PATENT DOCUMENTS

| | | | |
|---|---|---|---|
| 2,467,432 A | 4/1949 | Kesling | |
| 3,660,900 A | 5/1972 | Andrews | |
| 3,860,803 A | 1/1975 | Levine | |
| 3,916,526 A | 11/1975 | Schudy | |
| 3,922,786 A | 12/1975 | Lavin | |
| 3,950,851 A | 4/1976 | Bergersen | |
| 4,014,096 A | 3/1977 | Dellinger | |
| 4,195,046 A | 3/1980 | Kesling | |
| 4,324,546 A | 4/1982 | Heitlinger et al. | |
| 4,348,178 A | 9/1982 | Kurz | |

(Continued)

FOREIGN PATENT DOCUMENTS

EP 0091876 A1 10/1983

(Continued)

OTHER PUBLICATIONS

Alexander et al., "The DigiGraph Work Station Part 2, Clinical Management," JCO (Jul. 1990), pp. 402-407.

(Continued)

*Primary Examiner*—Cris L Rodriguez
*Assistant Examiner*—Heidi M Eide
(74) *Attorney, Agent, or Firm*—Brooks, Cameron & Huebsch, PLLC

(57) ABSTRACT

Systems and methods are disclosed for producing a digital model by providing a digital model of a tooth; providing a digital model of at least one attachment device having two or more portions, the digital model of the attachment device having the two or more portions extending through two or more surfaces of the tooth; and positioning the digital model of the attachment device on the digital model of the tooth to produce a combined computerized model.

14 Claims, 17 Drawing Sheets

U.S. PATENT DOCUMENTS

| | | |
|---|---|---|
| 4,478,580 A | 10/1984 | Barrut |
| 4,504,225 A | 3/1985 | Yoshii |
| 4,505,673 A | 3/1985 | Yoshii |
| 4,575,805 A | 3/1986 | Moermann et al. |
| 4,611,288 A | 9/1986 | Duret et al. |
| 4,656,860 A | 4/1987 | Orthuber et al. |
| 4,663,720 A | 5/1987 | Duret et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,837,732 A | 6/1989 | Brandestini et al. |
| 4,850,864 A | 7/1989 | Diamond |
| 4,856,991 A | 8/1989 | Breads et al. |
| 4,880,380 A * | 11/1989 | Martz ........................ 433/11 |
| 4,936,862 A | 6/1990 | Walker et al. |
| 4,937,928 A | 7/1990 | Van Der Zel |
| 4,964,770 A | 10/1990 | Steinbichler et al. |
| 4,975,052 A | 12/1990 | Spencer et al. |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,128,870 A | 7/1992 | Erdman et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,632 A | 9/1995 | Andersson et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,518,397 A | 5/1996 | Andreiko et al. |
| 5,533,895 A | 7/1996 | Andreiko et al. |
| 5,542,842 A | 8/1996 | Andreiko et al. |
| 5,549,476 A | 8/1996 | Stern |
| 5,587,912 A | 12/1996 | Andersson et al. |
| 5,605,459 A | 2/1997 | Kuroda et al. |
| 5,607,305 A | 3/1997 | Andersson et al. |
| 5,645,421 A | 7/1997 | Slootsky |
| 5,655,653 A | 8/1997 | Chester |
| 5,683,243 A | 11/1997 | Andreiko et al. |
| 5,733,126 A | 3/1998 | Andersson et al. |
| 5,740,267 A | 4/1998 | Echerer et al. |
| 5,815,154 A * | 9/1998 | Hirschtick et al. .......... 715/853 |
| 5,820,368 A * | 10/1998 | Wolk ............................ 433/3 |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,309,215 B1 | 10/2001 | Phan et al. |
| 6,398,548 B1 | 6/2002 | Muhammad et al. |
| 6,524,101 B1 | 2/2003 | Phan et al. |
| 6,554,611 B2 | 4/2003 | Chishti et al. |
| 6,830,450 B2 * | 12/2004 | Knopp et al. ................. 433/6 |
| 7,063,533 B2 * | 6/2006 | Phan et al. .................... 433/24 |
| 2002/0010568 A1 * | 1/2002 | Rubbert et al. ................. 703/6 |
| 2003/0152884 A1 * | 8/2003 | Wiechmann et al. .......... 433/9 |
| 2003/0198915 A1 * | 10/2003 | White .......................... 433/21 |
| 2003/0207224 A1 * | 11/2003 | Lotte ............................. 433/6 |
| 2005/0048433 A1 * | 3/2005 | Hilliard ....................... 433/24 |
| 2005/0106525 A1 * | 5/2005 | Knopp et al. ................. 433/6 |
| 2006/0223022 A1 * | 10/2006 | Solomon ....................... 433/6 |

FOREIGN PATENT DOCUMENTS

| | | |
|---|---|---|
| EP | 0299490 A2 | 1/1989 |
| EP | 0376873 A2 | 7/1990 |
| EP | 0490848 A2 | 6/1992 |
| EP | 0774933 B1 | 5/1997 |
| EP | 0541500 A1 | 6/1998 |
| EP | 0731673 B1 | 9/1998 |
| FR | 2369828 A1 | 6/1978 |
| FR | 2652256 A1 | 3/1991 |
| WO | WO 90/08512 A1 | 8/1990 |
| WO | WO 91/04713 A1 | 4/1991 |
| WO | WO 94/10935 A1 | 5/1994 |
| WO | WO 98/44865 A1 | 10/1998 |
| WO | WO 98/58596 A1 | 12/1998 |

OTHER PUBLICATIONS

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan.. 1979, Special Issue A, p. 221.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler, "3D Mapping of Maxillo-Facial Prosthesis," AADR Abstract#607,1980, 1 page total.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A Stereophotogrammetric System for the Detection of Prosthesis Loosening in Total Hip Arthroplasty", NATO Symposium on Applications of Human Biostereometrics, Jul. 9-13, 1978, SPIE vol. 166, pp. 112-123.

Baumrind et al., Mapping the Skull in 3-D, Reprinted from the Journal, *California Dental Association*, vol. 48, No. 2 (1972 Fall Issue) 11 pages total.

Baumrind, "A System for Craniofacial Mapping Through the Integration of Data from Stereo X-Ray Films and Stereo Photographs," An Invited paper submitted to the 1975 American Society of Photogram. Symposium on Close-Range Photogram. Systems, University of Ill., Aug. 26-30, 1975, pp. pp.142-166.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard at al., "Computerized Diagnosis in Orthodontics for Epidemiological Studies: A Progress Report", Abstracts of Papers, *Journal of Dental Research*; vol. 67, Special Issue Mar. 9-13, 1988, p. 169.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized Analysis of Occlusion in the Postcanine Dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Boyd et al., "Three Dimensional Diagnosis and Orthodontic Treatment of Complex Malocclusions Wlith the Invisalign Appliance", *Seminars in Orthodontics*, vol. 7, No. 4 (Dec. 2001), p. 274-293.

Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.

Brook et al. An Image Analysis System for the Determination of Tooth Dimensions from Study. Casts: Comparison with Manual Measurements of Mesio-distal Diameter, *J Dent Res.*, vol. 65, No. 3, Mar. 1986, pp. 428-431.

Burstone (interview), "Dr. Charles J. Burstone on The Uses of the Computer in Orthodontic Practice (Parts1 and 2)," *Journal of Clinical Orthodontics*, (Part 1) vol. 8, No. 7 , Jul. 1979; (Part 2) vol. 8, No. 8 pp. 539-551, Aug. 1979.

Burstone et al., "Precision Adjustment of the Transpalatal Lingual Arch: Computer Arch Form Predetermination," *Am. Journal of Orthodontics*, vol. 79, No. 2 (Feb. 1981), pp. 115-133.

Chaconas et al., "The DigiGraph Work Station, Part 1, Basic Concepts," JCO (Jun. 1990), pp. 360-367.

Chafetz et al., "Subsidence of the Femoral Prosthesis, a Stereophotogrammetric Evaluation," *Clinical Orthopaedics and Related Research*, No. 201 (Dec. 1985), pp. 60-67.

Chiappone, "Constructing the Gnathologic Setup and Positioner" *J. Clin. Orthod.*, 14:121-133, 1980.

Cottingham, "Gnathologic Clear Plastic Positioner" *Am. J. Orthod.*, vol. 55, No. 1, ( Jan. 1969),. pp. 23-31.

Crawford, "Computers in Dentistry: Part 1: CAD/CAM: The Computer Moves Chairside," "Part 2: F. Duret—A Man With A Vision," "Part 3: The Computer Gives New Vision- Literally," "Part 4: Bytes 'N Bites" The Computer Moves From the Front Desk to the Operatory, *Canadian Dental Journal*, vol. 54(9), (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Cureton, "Correcting Malaligned Mandibular Incisors With Removable Retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM DCS Titan System' for Production of Crowns/Bridges" *DSC Production AG*, Jan. 1992, pp. 1-7.

Defranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 2 pages total.

DenTrac Corporation, Dentrac document, pp. 4-13.

Duret et al, "CAD-CAM in Dentistry," *Journal of the American Dental Association*, vol. 117 (Nov. 1988), pp. 715-720.

Duret et al., "CAD/CAM Imaging in Dentistry," *Current Opinion in Dentistry*, vol. 1 (1991), pp. 150-154.

Duret, "Vers une prosthese informatisee," (English translation also attached), *Tonus*, vol. 75, (Nov. 15, 1985), pp. 55-57.

Duret, "The Dental CAD/CAM, General Description of the Project," *Hennson International Product Brochure*, Jan. 1986., 18 pages total.

Economides, "The Microcomputer in the Orthodontic Office," *JCO*, (Nov. 1979), pp. 767-772.

Elsasser, "Some Observations on the History and Uses of the Kesling Positioner" *Am. J. Orthod.*, vol. 36, No. 5, (May 1950) pp. 368-374.

Faber et al.,"Computerized interactive orthodontic treatment planning," *Am. J. Orthod.*, vol. 73, No. 1 (Jan. 1978), pp. 36-46.

Felton et al. "A computerized analysis of the shape and stability of mandibular arch form" *Am. Journal of Orthodontics and Dentofacial Orthopedics*, vol. 92, No. 6 (Dec. 1987), pp. 478-483.

Friede et al., "Accuracy of Cephalometric Prediction in Orthognathic Surgery," Abstract of Papers, *Journal of Dental Research*, vol. 70 (1987), pp. 754-760.

Gim-Alldent Deutschland, "Das DUX System: Die Technik" 2 pages total.

Grayson, "New Methods for Three Dimensional Analysis of Craniofacial Deformity," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5-6.

Guess et al., "Computer Treatment Estimates in Orthodontics and Orthognathic Surgery, ",*JCO*, (Apr. 1989), pp. 262-28.

Heaven et al., "Computer-based Image Analysis of Artificial Root Surface Caries," Abstracts of Papers, *Journal of Dental Research*, vol. 70,Apr. 17-21, 1991, p. 528.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

JCO Interviews, "Craig Andreiko , DDS, MS on the Elan and Orthos Systems", *JCO*, (Aug. 1994), pp. 459-468.

JCO Interviews, "Dr. Homer W. Phillips on Computers in Orthodontic Practice, Part 2," *JCO*, (Dec. 1983), pp. 819-831.

Jerrold, "The Problem, Electronic Data Transmission and the Law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case Reports on Tooth Positioners Using LTV Vinyl Silicone Rubber" J. Nihon University School of Dentistry, 26(1):11-29, 1984.

Kamada et al., "Construction of Tooth Positioners With LTV Vinyl Silicone Rubber and Some Case Reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res.* , vol. 63, No. 11 (Nov. 1984), pp. 1298-1301.

Kesling, "Coordinating the Predetermined Pattern and Tooth Positioner With Conventional Treatment" *Am. J. Orthod. Oral. Surg.*, 32:285-293, 1946.

Kesling, "The Philosophy of the Tooth Positioning Appliance" *Am. J. Orthod. Oral. Surg.*, 31(6):297-304, 1945.

Kleemann et al., "The Speed Positioner" *J. Clin. Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal of the American Dental Assoc.*, vol. 118, No. 6 (Jun. 1989), pp. 703-707.

Manetti et al., "Computer-aided Cefalometry and New Mechanics in Orthodontics" (Article Summary in English, article in German), *Fortschr. Kieferorthop*. 44, 370-376 (Nr. 5), 1983.

McCann, Inside the ADA, *Journal of the American Dental Assoc.*, vol. 118 (Mar. 1989) pp. 286-294.

McNamara et al., "Invisible Retainers", *J. Clinical Orthodontics*, (Aug. 1985) pp. 570-578.

McNamara et al., Chapter 19: Invisible Retainers, *Orthodontic and Orthopedic Treatment in the Mixed Dentition*, Needham Press, Jan. 1993. pp. 347-353.

Moermann et al., "Computer Machined Adhesive Porcelain Inlays: Margin Adaptation after Fatigue Stress," IADR Abstract 339, *Journal of Dental Research*, vol. 66(a) (1987), p. 763.

Mörmann et al., "Marginal Adaptation von adhasiven Porzellaninlays in vitro," *Schwizerische Monatsshrift fur Zahnmedizin*, vol. 85 (1985), p. 1118-1129.

Nahoum, "The Vacuum Formed Dental Contour Appliance" *The New York State Dental Journal*, 30(9):385-390, Nov. 1964.

Nash, "CEREC CAD/CAM Inlays: Aesthetics and Durability in a Single Appointment," *Dentistry Today*, (Oct. 1990), pp. 20, 22-23, 54.

Nishiyama et al., "A New Construction of Tooth Repositioner by LTV Vinyl Silicone Rubber" J. Nihon University School of Dentistry, 19(2):93-102, 1977.

Pinkham, "'Foolish' Concept Propels Technology," *Dentist*, Jan./Feb. 1989, 3 pages total.

Pinkham, "Inventor's CAD/CAM May Transform Dentistry," *Dentist*, Sep. 1990, 3 pages total.

Ponitz, "Invisible Retainers", *Am. J. Orthodontics*, vol. 59, No. 3, Mar. 1971, pp. 266-272.

Procera Research Projects, *PROCERA Research Projects* 1993—Abstract Collection, 1993, pp. 3-24.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, "Feasibility of an Automated System for Production of Dental Restorations," PhD Thesis, Univ. of Minnesota, Nov. 1988, 244 pages total.

Richmond et al., Research Reports, "The Development of a 3D Cast Analysis System," *British Journal of Orthodontics*, vol. 13, No. 1, (Jan. 1986) pp. 53-54.

Richmond, "Recording the Dental Cast in Three Dimensions," *Am. J. Orthod. Dentofac. Orthop.*, vol. 92, No. 3, (Sep. 1987), pp. 199-206.

Rudge, "Dental arch analysis: Arch Form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computed Tomography in Maxillofacial Surgical Planning," *Arch Otolamgol Head Neck Surg.* vol. 114 (Apr. 1988), pp. 438-442.

Shilliday, "Minimizing Finishing Problems With the Mini-Positioner" *Am. J. Orthod.* 59:596-599, 1971.

Siemens, "CEREC—Computer-Reconstruction," High Tech in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050342, filed Jun. 20, 1997, 41 pages total.

Van Der Linden et al., "Three-Dimensional Analysis of Dental Casts by Means of the Optocom," *J Dent Res*, Jul.-Aug. 1972, vol. 51, No. 4, p. 1101.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Varady et al., Reverse Engineering of Geometric Models—An Introduction. Computer-Aided Design, 29 (4):255-268, 1997.

Warunek et al., "Clinical Use of Silicone Elastomer Appliances" *JCO*, MH (10):694-700, 1989.

Warunek et al., "Physical and Mechanical Properties of Elastomers in Orthodontic Positioners" *Am. J. Orthod. Dentofac. Orthop.*, 95:388-400, 1989.

Wells, "Application of the Positioner Appliance in Orthodontic Treatment" *Am. J. Orthodont.*, 58:351-366, 1970.

Williams, "Dentistry and CAD/CAM: Another French Revolution," *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical Measurement of Dental Cast Profile and Application to Analysis of Three-Dimensional Tooth Movement in Orthodontics," *Frontiers in Med. and Biol. Eng'g*, vol. 1, No. 2 (1988), pp. 119-130.

Product Brochure, Raintree Essix, Inc., New Orleans, Louisiana 70125, 7 pages total from http://www/essix.com/maaazine/default.html.

Product Brochure, Tru-tain Orthodontic & Dental Supplies, Rochester, Minnesota 55902, 16 pages total.

\* cited by examiner

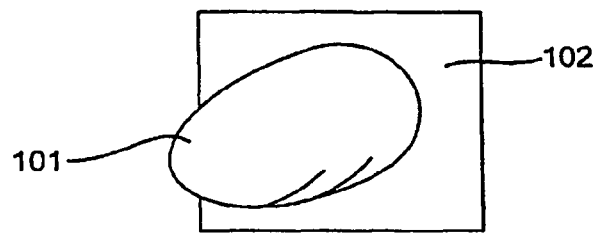
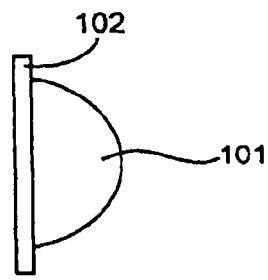
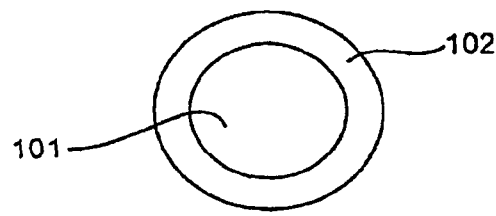
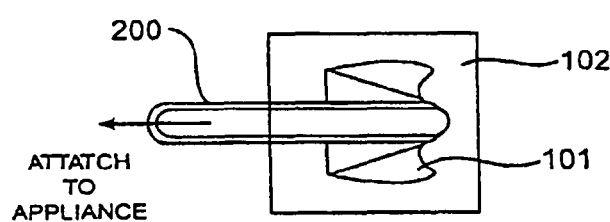
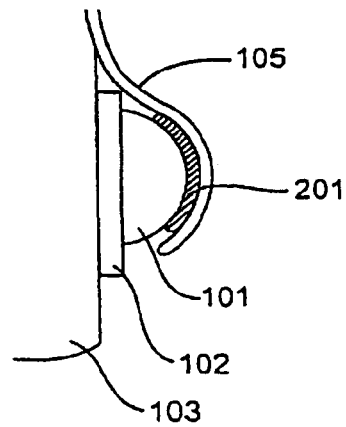

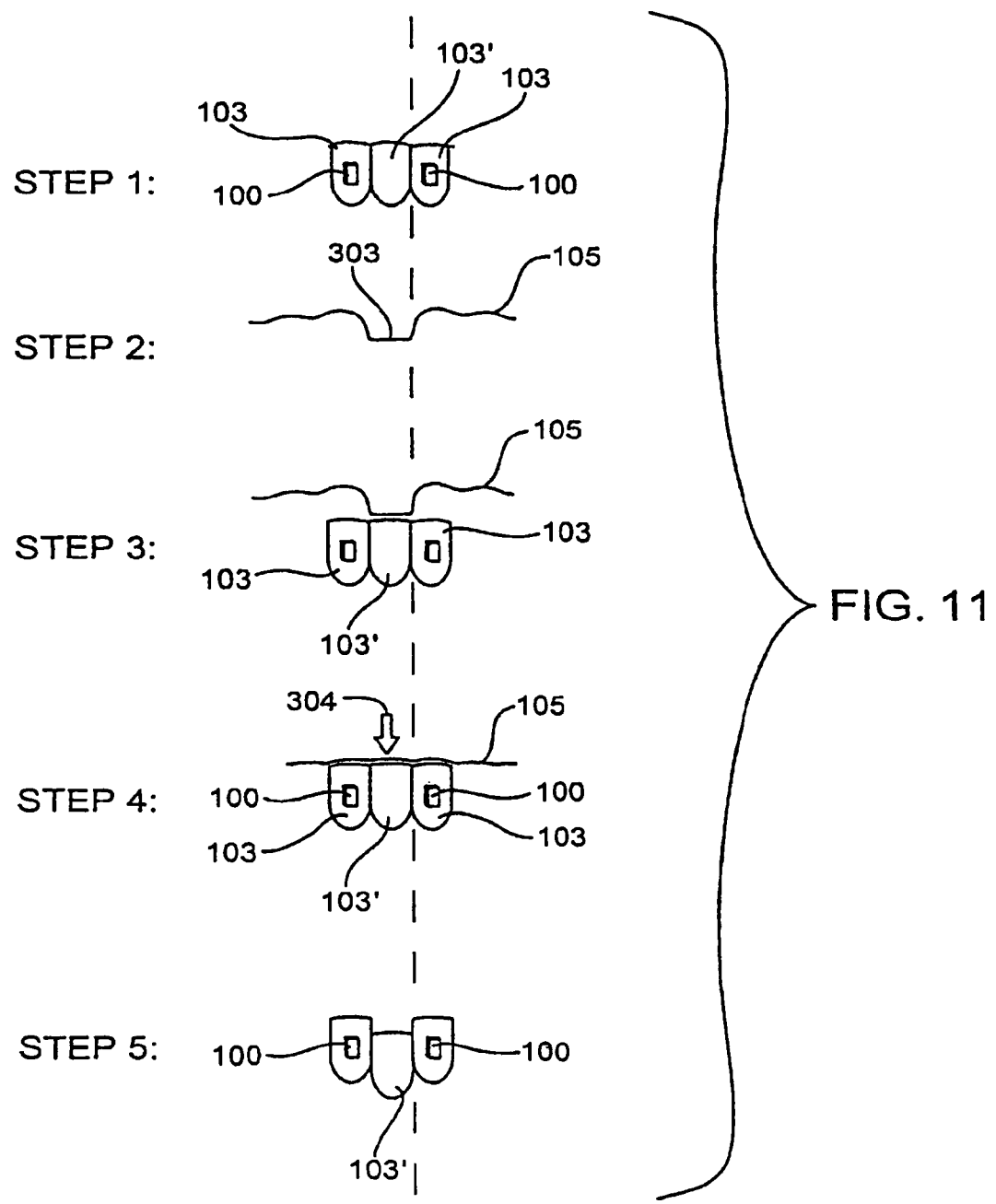

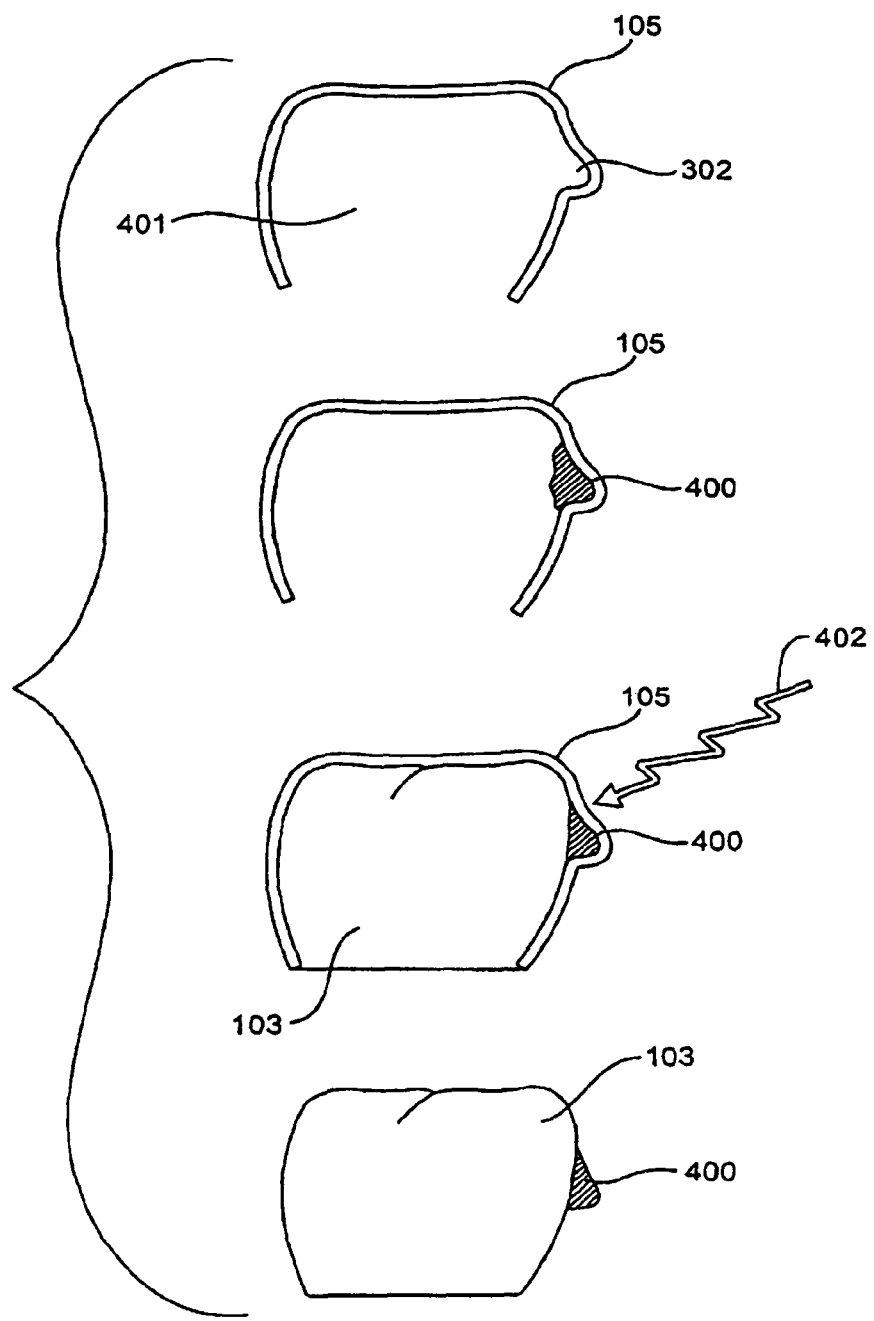

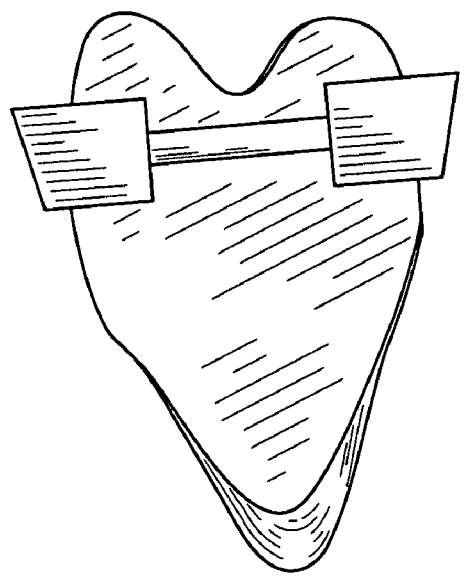 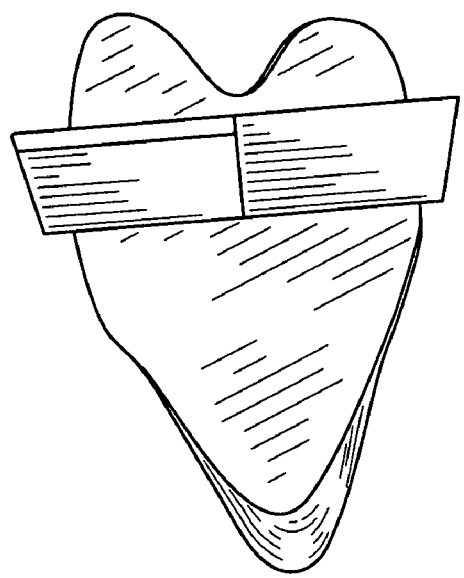
FIG. 21A  FIG. 21B
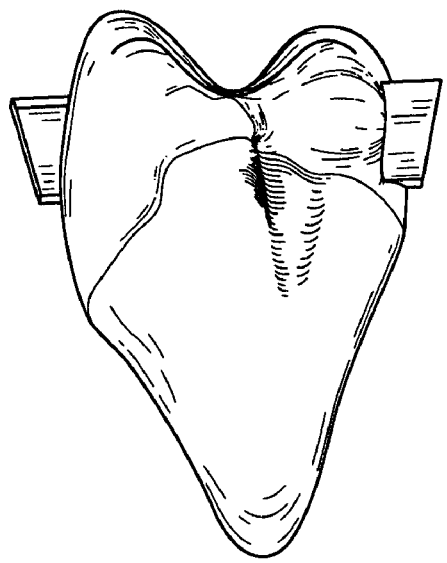
FIG. 21C

POLAR ATTACHMENT DEVICES AND METHOD FOR A DENTAL APPLIANCE

CROSS-REFERENCES TO RELATED APPLICATIONS

This application is a continuation-in-part of application Ser. No. 10/632,482, filed on Aug. 1, 2003, now U.S. Pat. No. 7,059,850 which is a continuation-in-part of application Ser. No. 10/040,269, filed on Oct. 29, 2001, now U.S. Pat. No. 6,705,863, the full disclosures of each of these applications which are incorporated herein by reference herein.

BACKGROUND OF THE INVENTION

The present invention is related generally to the field of orthodontics. More particularly, the present invention is related to improved systems and methods for removably attaching a dental positioning appliance to the dental features of a patient during orthodontic treatment.

Orthodontic treatments involve repositioning misaligned teeth and improving bite configurations for improved cosmetic appearance and dental function. Repositioning teeth is accomplished by applying controlled forces to the teeth over an extended period of time. This is conventionally accomplished by wearing what are commonly referred to as "braces." Braces comprise a variety of appliances such as brackets, bands, archwires, ligatures, and O-rings. The brackets and bands are bonded to the patient's teeth using a suitable material, such as dental adhesive. Once the adhesive has set, the archwire is attached to the brackets by way of slots in the brackets. The archwire links the brackets together and exerts forces on them to move the teeth over time. Twisted wires or elastomeric O-rings are commonly used to reinforce attachment of the archwire to the brackets. Attachment of the archwire to the brackets is known in the art of orthodontia as "ligation" and wires used in this procedure are called "ligatures." The elastomeric O-rings are called "plastics."

After the archwire is in place, periodic meetings with the orthodontist are required, during which the patient's braces will be adjusted. This involves installing different archwires having different force-inducing properties or by replacing or tightening existing ligatures. Between meetings, the patient may be required to wear supplementary appliances, such as elastic bands or headgear, to supply additional or extraoral forces.

Although conventional braces are effective, they are often a tedious and time consuming process requiring many visits to the orthodontist's office. Moreover, from a patient's perspective, they are unsightly and uncomfortable. Moreover, the archwire and ligatures which connect the brackets in a continuous network make brushing, flossing between the teeth and other dental hygiene procedures difficult, possibly contributing to the development of gingivitis. Consequently, alternative orthodontic treatments are needed. In particular, it would be desirable to use appliances which can be removed by the patient during daily dental hygiene routines, while participating in athletic activities, or for cosmetic purposes.

A particularly promising approach relies on the use of elastic positioning appliances for realigning teeth. Such appliances comprise a thin shell of elastic material that generally conforms to a patient's teeth but is slightly out of alignment with the initial tooth configuration. Placement of the elastic positioner over the teeth applies controlled forces in specific locations to gradually move the teeth into the new configuration. Repetition of this process with successive appliances comprising new configurations eventually move the teeth through a series of intermediate configurations to a final desired configuration. A full description of an exemplary elastic polymeric positioning appliance is described in U.S. Pat. No. 5,975,893, and in published PCT application WO 98/58596 which designates the United States and which is assigned to the assignee of the present invention. Both documents are incorporated by reference for all purposes.

In addition to their ease of use, polymeric positioning appliances are generally transparent, providing an improved cosmetic appearance, and impart substantial force on the teeth, due to stiffness of the appliance. The stiffness of an elastic positioning appliance is a result of the modulus of the thermoformable polymer materials from which it is made. The higher the modulus of the materials, the higher the stiffness of the appliance. When a patient positions such an appliance over a prescribed group of teeth, one or more of the teeth will provide a base or anchor region for holding the positioning appliance in place while the stiffness of the polymeric material will impart a resilient repositioning force against one or a portion of the remaining teeth. By designing the appliance to cover the teeth, a much larger contact surface area is afforded compared to traditional spring retainers and wire-based appliances. However, such anchoring and repositioning abilities of removable elastic positioning appliances are still dependent on the physical features and configuration of the patient's teeth, palette, and previous dental work, to name a few. For example, shell-like elastic polymeric positioning appliances have difficulty applying certain forces to individual teeth, such as extrusive force (e.g., pulling or raising a tooth relative to the jaw).

Thus, it would be desirable to provide tooth positioners, systems, and methods which apply adequate force in desired directions to selected teeth at specific times during treatment. In particular, it would be desirable to enable the fabrication and use of removable positioners and systems which can apply extrusive, rotational, and other directional forces which have heretofore been difficult to apply with removable positioners. It would also be desirable to reduce the cost of the orthodontic treatment and retain the patient benefits of a removable appliance in cases where they might not otherwise be available. At least some of these objectives will be met by the designs and methods of the present invention described hereinafter.

SUMMARY OF THE INVENTION

The present invention provides improved devices, systems and methods for removably attaching a polar dental positioning appliance to the dental features of a patient during orthodontic treatment.

In one aspect, a polar attachment has two or more ends that have a fixed spatial or planar relationship between the buccal and lingual portions. The buccal and lingual portions need not have the same geometry. A specific positional relationship between buccal and lingual ends can be effected when the attachment is placed on the tooth. In this embodiment, a polar attachment is one body that passes through a target tooth to create both a buccal and lingual geometry at the same time with specific, set relative positions.

In another aspect, a polar attachment is one body that passes through a target tooth to create both an occlusal or incisal and either a buccal or a lingual geometry at the same time with specific, set relative positions.

In another aspect, a polar attachment is one body that passes through a target tooth to create both an occlusal and an incisal geometry at the same time with specific, set relative positions.

In yet another aspect, systems and methods are disclosed for producing a digital model by providing a digital model of a tooth; providing a digital model of at least one attachment device having two or more portions, the digital model of the attachment device having the two or more portions extending through two or more surfaces of the tooth; and positioning the digital model of the attachment device on the digital model of the tooth to produce a combined computerized model.

Advantages of such attachments include greater accuracy and less operator training. Further, one attachment body is used in place of what now requires two separate bodies. The result is time savings on the operator in placing as well as aligning two separate bodies.

Specific design and location of the polar attachment devices may provide newly achievable and/or more effective repositioning forces, anchoring ability and appliance retention. The systems and methods of the present invention provide the design, production and use of such attachment devices with removable dental positioning appliances in orthodontic treatment.

The use of attachment devices in combination with removable dental positioning appliances provides the patient with the benefits of removable appliances while retaining the ability to extrude, rotate, and otherwise manipulate teeth as with conventional braces. Like conventional braces, attachment devices may be bonded to the surface of the teeth in order to provide physical features which facilitate the application of controlled force. The attachment devices of the present invention may have a very simple construction, in some instances being only a bump, bead, wedge, or other body or structure which can be fixedly attached to the surface of a tooth or other dental feature in order to transmit force generated by the dental positioning appliance to the dental feature and/or to anchor the positioning appliance to teeth in order to permit the appliance to apply forces elsewhere in the patient's teeth. In such instances, the attachment device acts as a handle or lever to assist in the transmission of force between the teeth and the dental positioning appliance. In other instances, the attachment device may feature a hook, similar in design to those used for mounting elastic bands. The hook may be engaged with a number of ligatures, bands, filaments, coils or other connecting members to effect repositioning of the teeth, usually in combination with the dental positioning appliance. The hook may serve as an anchor in the repositioning of other teeth, or it may serve to apply directed force to the surface of the tooth to which it is bonded.

The attachment devices of the present invention, unlike conventional braces, are typically small, infrequent, (i.e., present on very few of the patient's teeth) unnoticeable to others, and do not interfere with dental hygiene practices. Usually, the attachment device will have a small base e.g., up to 4 mm across (mesial-distal) and up to 6 mm long (gingiva-crown). An attachment device body may typically protrude up to a maximum of 2.5 mm. This is significantly smaller than standard brackets or bands used in convention braces which may protrude up to 4 mm. The devices may be bonded in specific locations throughout the dentition where appropriate and this may only be required at one or a few locations. Thus, the infrequency of the device, in addition to the size, also reduces its visibility and awareness to the patient. Likewise, the attachment device may be bonded to any surface of the teeth, including lingual surfaces which would allow the devices to be largely unnoticeable to others. In these cases, shape and design considerations would prevent any irritation to the contacting tissues, such as the tongue, inner lip and inner cheek. When placed in visible areas, the attachment device may be color matched to the dental surface to further diminish its visibility. In addition, such attachment devices are typically designed to work with a removable dental appliance. Thus, when the appliance is removed, routine brushing, flossing and dental care may be undertaken in the usual manner.

Brackets used with conventional braces, such as those used to support elastic bands or headgear, are limited in design. Generally, these attachment devices have a large profile, protruding 2-4 mm, which is not conducive to use with elastic positioning appliances or other devices designed to be removably positioned over the attachment device. Likewise, their surface geometry is limited to a few prescribed functions which are specific to use with conventional braces. Thus, they are not adequately capable of providing functions necessary to the present invention, such as removably attaching a dental positioning appliance.

In a first aspect of the present invention, the attachment devices are comprised of an attachment body having a base. The base may simply be the portion of the attachment body which will be bonded to the surface of the dental feature. Alternatively, the base may be an enlarged portion of the body, designed to increase the surface area of the bond. Likewise, the base may be removable or permanently attached. The attachment body may feature a variety of designs, most commonly being bumps, beads, wedges, also including but not limited to hooks, clasps, bands, brackets, buttons, snaps, springs, levers, rods, tubes, coils, indents and/or other protrusions. Each design may serve one or a number of purposes in repositioning of the teeth. For example, a clasp may be used to attach a portion of a removable positioning appliance to the attachment device. This attachment device design may be desired for anchoring of the appliance or applying force to the dental feature to which the attachment device is bonded. Additional devices may be used in conjunction with the attachment body to attach the appliance to the attachment device. For example, adhesives, flexible bands or connecting ligatures may be used in conjunction with the design of the attachment body to aid in connection to the appliance. In one such case, an attachment body located on the lower jaw may be attached to a removable appliance placed on the upper jaw by means of a flexible band. This may afford desired force vectors that are unobtainable by other means. Alternatively, the attachment body may be comprised of specific design features to aid in properly seating a removable elastic repositioning appliance, in addition to anchoring the appliance in place to apply repositioning forces. A preferred embodiment of these design features includes an attachment body with a sloping face, e.g., a wedge.

The phrase "dental feature" will apply to any portion of the patient's teeth which may be contacted by a dental positioning appliance and/or engaged by an attachment device. Usually, the dental feature will be a portion of a surface of a natural tooth, but in some instances could be a portion on a surface of an artificial tooth, e.g., a dental implant, or a non-natural surface or a repaired surface of a native tooth, e.g., a filling, crown, inlay, restoration, or the like. Thus, the phrase dental feature will generally refer to all natural and non-natural teeth in a patient's dentition. In a second aspect of the present invention, the attachment device is bonded to and/or formed over a dental feature in a desired location. The attachment device may be bonded to any of these features with any suitable bonding material, typically dental restorative composites. The location in which one or more of these attachment devices are bonded is dependent upon the desired repositioning goal. The devices may be bonded to any surface of the dental features and may be placed singly or in groups. Likewise, a given attachment device may be bonded to surfaces of more than one dental feature. In a preferred embodiment, an attachment device may be placed on each of two teeth located on opposite sides of one or a contiguous group of teeth. When an elastic positioning appliance is inserted and attached to the two attachment devices, an intrusive force may be applied to the tooth or teeth in between. This is counterintuitive to the methods of conventional orthodontics in which brackets are bonded to the teeth that require repositioning.

In a third aspect of the present invention, the attachment devices may be constructed from variety of materials, including but not limited to metals, glass or silicone filled polymers, and other composite materials. Such materials are typically designed to be chip, break and shear resistant for durability. The base of the attachment device may be constructed from the same or from different materials as the attachment body. Likewise, the attachment body may be permanently or removably mounted on the base or the body and base may be constructed as one entity.

In a preferred embodiment, the attachment device may be constructed from a polymer material or combination of materials which have been formulated to be sensitive to an environmental condition or external stimulus. Upon exposure to such a condition or stimulus, the material may undergo a predetermined state change, which may be temporary or permanent. For example, upon exposure, a rigid material may become temporarily malleable, allowing changes in geometry to be made. Upon removal of the condition or stimulus, the material may return to its original rigid state and geometry or it may return to its original rigid state with the new geometry. In the former case, such stimulus may be used to facilitate coupling an attachment device to an elastic positioning appliance. The stimulus may alter the geometry of the attachment device during insertion and placement of the appliance. Removal of the stimulus may allow the device to return to its original geometry for application of repositioning forces. A full description is provided in application U.S. Pat. No. 6,183,248, the full disclosure of which is incorporated herein by reference. In the latter case, such stimulus may be used to facilitate bonding of the attachment device to the surface of the dental feature. The stimulus may alter the state and geometry of the attachment device, or simply the base, to conform it to the surface of the dental feature to which it is to be bonded. Upon removal of the stimulus, the attachment device may remain in the new geometry, providing a larger contact surface area for bonding.

Similarly, a malleable material may be molded into a desired form and polymerized by exposure to an environmental condition or stimulus. Such polymerization may permanently hold the material in the desired form. This may be useful in both constructing the attachment device and bonding the device to a dental surface. For example, malleable material may be inserted into a mold of an attachment device. Polymerization, as described above, may result in a rigid attachment device in the molded form. In a preferred embodiment, the mold of the attachment device may be an impression in the wall of an elastic positioning appliance. This may ensure proper surface geometry for association between the attachment device and the appliance. Likewise, polymerization of the material while the appliance is in place over the dental features may simultaneously bond the attachment device to the dental feature. This may ensure proper alignment of the attachment device and the receiving impression in the appliance, and it may also preclude the need for additional bonding materials.

In a fourth aspect of the present invention, methods are provided to produce and/or bond an attachment device to a dental feature. Three preferred embodiments are applicable for use with elastic repositioning appliances or similarly fabricated devices and are as follows: 1) basic casting, 2) casting with polymerizing material and 3) computer-aided casting with polymerizing material. An example of basic casting involves producing two identical attachment devices by any means and comprised of any material(s). One attachment device may be placed in a desired location on a dental surface of the patient. The other attachment device may be placed in the identical location on a mold replicating at least the dental surface. An elastic positioning appliance or similar device may be formed over the mold containing the attachment device. Upon removal, a negative impression of the attachment device may be seen in the wall of the elastic positioning appliance. Therefore, when the appliance is inserted and seated in position by the patient, the impression in the appliance will correspond with the attachment device bonded to the dental surface. If the attachment device is to be used as a point to effect movement of the dental feature to which it is attached, the attachment device may be bonded to the dental feature in a position or orientation that differs from the mold. Therefore, when the appliance is inserted by the patient, the impression in the appliance will be slightly out of alignment with the attachment device. This will apply force to the attachment device, resulting in gradual repositioning of the device and underlying dental feature.

The method of casting with polymerizing material is similar to basic casting. Like basic casting, an attachment device of any design and material is placed in a desired location on a mold replicating at least the dental surface of interest. Again, an elastic positioning appliance or similarly fabricated device may be formed over the mold containing the attachment device, creating a negative impression of the attachment device in the wall of the appliance. At this point, a malleable polymerizing material may be placed into the negative impression in the appliance. When the appliance is inserted and seated in position in the oral cavity, the polymerizing material will be in contact with the dental surface and will be in the proper position. The material may be polymerized by any means, typically by an external stimulus or environmental condition. Polymerization may simultaneously harden the material and bond the material to the dental surface. Upon removal of the appliance, the formed attachment device may remain in place on the dental surface.

The method of computer-aided casting with polymerizing material is similar to the methods described above, yet differs in the steps of creating the appliance. Here, a 3-D computerized image of the attachment device is virtually placed in a desired location on an image of the dental surface. A mold is produced from the images using any computer-guided model fabrication system, such as stereolithography, CNC machining, and laser machining. The result is a mold of at least the dental surface of interest with a replica of the attachment device in proper position. At this point, an elastic positioning appliance or similarly fabricated device may be formed over the mold containing the attachment device, creating a negative impression of the attachment device in the wall of the appliance. Again, a malleable polymerizing material may be placed into the negative impression in the appliance. When the appliance is inserted and seated in position in the oral cavity, the material may be polymerized, leaving a formed attachment device in place on the dental surface when the appliance is removed.

In a fifth aspect of the present invention, an additional method is provided to produce and/or bond an attachment device to a dental feature. Two preferred embodiments are applicable for use with any dental appliances. The first embodiment involves a multi-tooth template which may be used to produce and/or bond an attachment device to a dental feature. The multi-tooth template may be thin and flexible to fit over multiple dental features at once, allowing multiple attachment devices to be placed at the same time. Receptacles may be present in the template to receive a polymerizing material. When the template is inserted and seated in position in the oral cavity, the polymerizing material will be in contact with the dental surface and will be in the proper position. The material may be polymerized by any means, typically by an external stimulus or environmental condition. Polymerization may simultaneously harden the material and bond the material to the dental surface. Upon removal of the template, the formed attachment device may remain in place on the dental surface. This method may be similar or identical to casting with polymerizing material and computer-aided casting with polymerizing material, however it may differ in that the template may not be used as the repositioning appliance. This difference may afford the use of template designs that are not applicable to repositioning appliances. For example, the template may be comprised of a material that is unsuitable for a repositioning appliance, or it may contain additional design features, such as handles, that would interfere with such usage. Similarly, the template may be fabricated from a mold of the patient's present tooth configuration, rather than the tooth configuration prescribed by an elastic positioning appliance. This may facilitate the method of attachment device production and/or bonding due to the closer fit of the template to the tooth configuration.

The second embodiment involves a single-tooth template which may be used to produce and/or bond an attachment device to a dental feature. The single-tooth template may be more rigid and may fit over a single dental feature. The template may be comprised of one or more receptacles to receive polymerizing material. When applied to the target surface of the dental feature, the material may be polymerized by any means previously described. The resulting attachment device is properly shaped and bonded in place. Alternatively, the single-tooth template may be comprised of a receptacle that is rigid, to receive the polymerizing material, surrounded by a thin, film-like portion of material that conforms to the dental feature. The thin, flexible area may contain an adhesive with which to hold the template in place on the dental feature. The material may then be polymerized to form the attachment device. When the procedure is complete, the template may be peeled off and discarded.

Single-tooth and multi-tooth templates may allow the production and placement of one or more attachment devices to a dental feature independent of the geometry of certain adjacent dental features. Thus, a template may be used throughout various stages of orthodontic repositioning treatment. This may be useful to replace an attachment device which has broken off mid-treatment or to place new attachment devices throughout treatment. As described above, at least one receptacle may be present in the template to receive a polymerizing material. When the template is inserted and seated in position in the oral cavity, the polymerizing material will be in contact with the dental surface and will be in the proper position. The material may be polymerized by any means, typically by an external stimulus or environmental condition. Polymerization may simultaneously harden the material and bond the material to the dental surface. Upon removal of the template, the formed attachment device may remain in place on the dental surface. Alternatively, templates may be used to bond any attachment device to a dental feature surface. For example, a pre-fabricated attachment device may be bonded to a surface with the use of a template. An attachment device may be inserted in a receptacle of a template, adhesive applied to the base of the attachment device and the template applied to the dental surface. After bonding has occurred, the template may be removed. Thus, the template may provide proper positioning and orientation. Likewise, a template may be used to form an attachment device using a polymerizing material, and then used again to bond the attachment device to a dental surface.

In a sixth aspect of the present invention, a method is provided to improve the production of templates or elastic positioning appliances. In a preferred embodiment, additional structures are provided in the mold of the dental feature with a desired attachment device. The structures may be of any geometry and are typically placed near the gingival surface. When a template or appliance is thermoformed over the mold and additional structures, the structures provide a protrusion which aids in drawing the template or appliance from the mold. The protrusion may then be removed before use.

In a further aspect of the present invention, a method is provided to further improve the production of templates or elastic positioning appliances. In some cases, it may be desired to alter a template or appliance after it has been removed from a mold. Such alterations may include trimming edges or removing portions to prevent interference with specific devices or dental features. For example, it may be desirable to produce an elastic appliance with a window in a particular location corresponding to the placement of an attachment device. To ensure proper location of the window, a structure may be provided in the mold at the same location to aid in the creation of the window. In a preferred embodiment, a structure of spherical geometry may be provided in the mold at the desired location. Thermoforming of the appliance may result in a spherical protrusion at the location of the structure. After removal of the appliance from the mold, the spherical protrusion may be removed by cutting, filing, sawing, or any other means of removal. Thus, a window with a shape corresponding to the cross section of the structure, in this case a circle, may remain. As a result, a template or positioning appliance may be produced to cover desired dental features or to provide windows to expose such features.

BRIEF DESCRIPTION OF THE DRAWINGS

FIGS. 4 and 4A are top and side view, respectively, of an exemplary attachment device having a hemispherical attachment body in the form of a simple "bump."

FIG. 4B is a perspective view of a similar attachment device with an elongated attachment body.

FIG. 5 illustrates an attachment device having an elastic band connected to a hook portion thereof.

FIG. 6 illustrates an attachment device similar to that shown in FIG. 4 which is attached to a positioning appliance via an adhesive layer.

FIG. 11 illustrates a method according to the present invention for intruding a tooth located between a pair of teeth having attachment devices thereon.

FIG. 14D includes a series of cross-sectional views further describing the method of FIGS. 14A-14C.

FIG. 21A-21C shows cross-sectional views and perspective views of combined geometries of a tooth and a polar attachment.

DESCRIPTION

The present invention provides improved systems and methods for removably attaching a dental positioning appliance to the dental features of a patient during orthodontic treatment. Preferred embodiments involve elastic repositioning appliances or similarly fabricated devices, however the present invention is applicable to any type of removable appliance. Systems for removably attaching an appliance typically involve the use of one or more attachment devices positioned on at least one dental feature.

Figure 1:
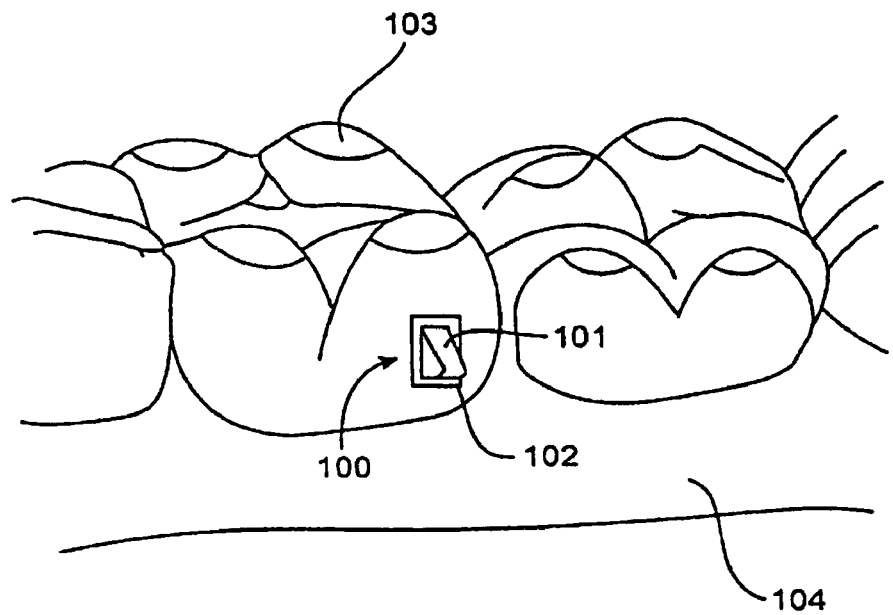
FIG. 1 illustrates a patient's tooth having an attachment device of the present invention bonded thereon.
Figure 2A:
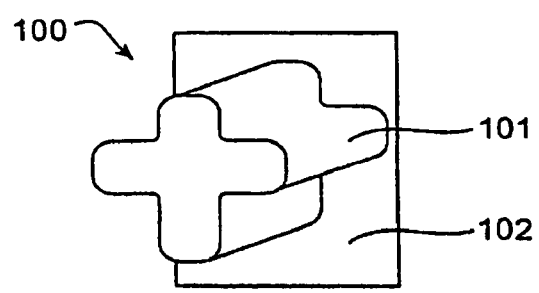
FIGS. 2A and 2B illustrate exemplary attachment devices having broad bonding bases attached thereto.
Figure 3A:
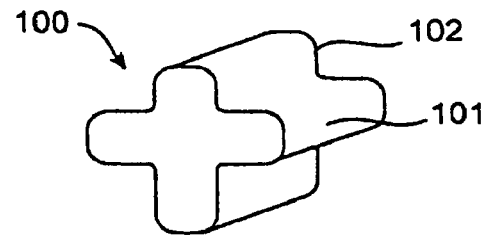
FIGS. 3A and 3B illustrate attachment devices similar to those illustrated in FIGS. 2A and 2B, except that the attachment base is integral with the attachment body.
Figure 2B:
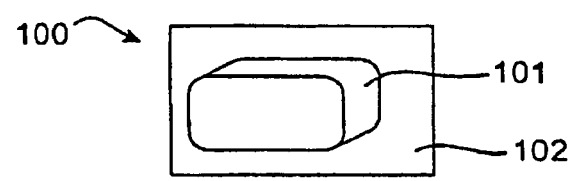
Figure 3B:
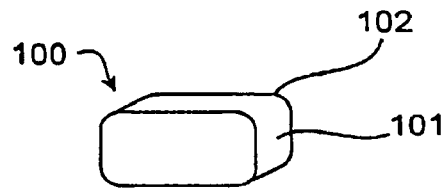

Referring to FIG. 1, a preferred embodiment of an attachment device 100 is shown bonded to a tooth 103 above the gingiva 104. The attachment device 100 may be comprised of an attachment body 101 having a base 102, which may be integral or separate and permanently or removably joined. Additional embodiments of attachment bodies 101 are depicted in FIGS. 2A-2B and FIGS. 3A-3B. As seen in FIGS. 2A and 2B, the attachment device 100 may have a base 102 which is broader than the attachment body 101 to increase bonding surface area. Alternatively, the base 102 may simply be an end of the attachment body 101 for direct bonding to the tooth 103. Corresponding embodiments with such bases 102 are depicted in FIGS. 3A and 3B. The devices 100 may be bonded to any surface of a dental feature and may be located in one or more locations.

Specific shapes and designs may be particularly useful in certain locations. For example, attachment devices 100 positioned on the lingual surfaces of the teeth would characteristically prevent irritation to contacting tissues, such as the tongue. FIGS. 4, 4A and 4B depict preferred embodiments of round-shaped attachment bodies 101 for such a purpose. A side view of such an attachment body 101 is shown in FIG. 4A. Bases 102 may be of any shape, thickness and orientation in relation to an attachment body 101. Likewise, a base 102 may have more than one discrete attachment body 101.

Additional devices may be used in conjunction with an attachment body 101 to attach an appliance to the tooth 103. For example, adhesives, flexible bands or connecting ligatures may be used in conjunction with the design of the attachment body 101 to aid in connection to the appliance. FIG. 5 depicts an attachment body 101 with a flexible band 200 to attach the body 101 to an appliance (not shown). The body 101 is shaped so as to receive the band 200 and hold it in place, for example in a hook shape. FIG. 6 is side view illustrating an attachment body 101 with an adhesive 201 to aid in attachment to an appliance 105. Such an adhesive 201 may be any type of biocompatible material which may be applied by the patient, provided by the attachment body 101 or provided by the appliance 105. Likewise, the adhesive 201 may provide adhesive qualities over variable lengths of time.

Figure 7:
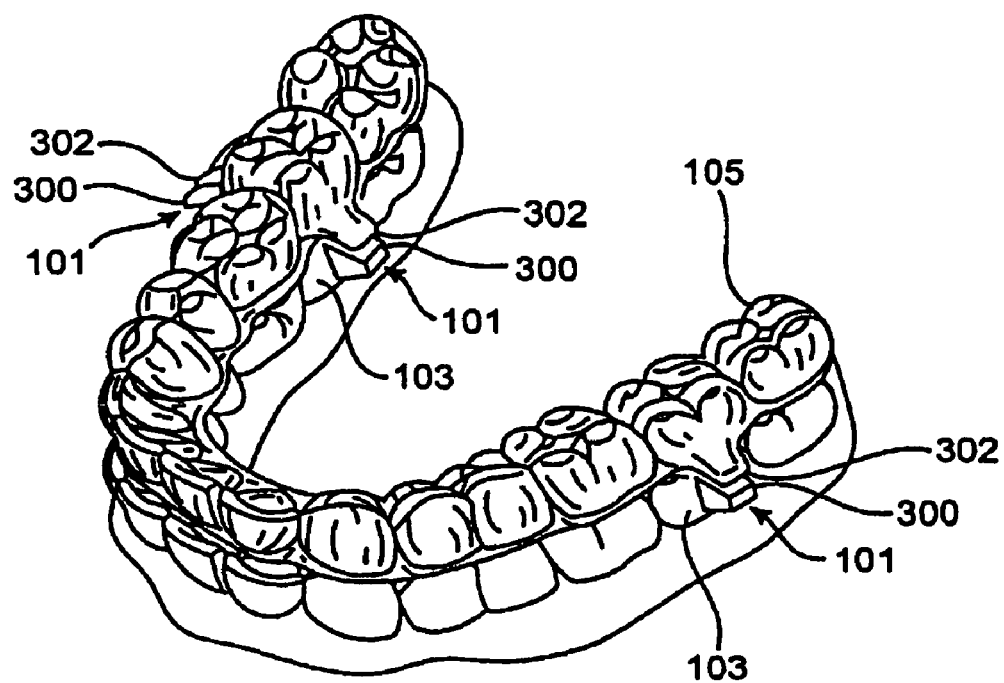
FIG. 7 illustrates an exemplary wedge-shaped attachment device of the present invention in combination with a dental positioning appliance having cavities formed therein for removably receiving the attachment devices.
Figure 8:
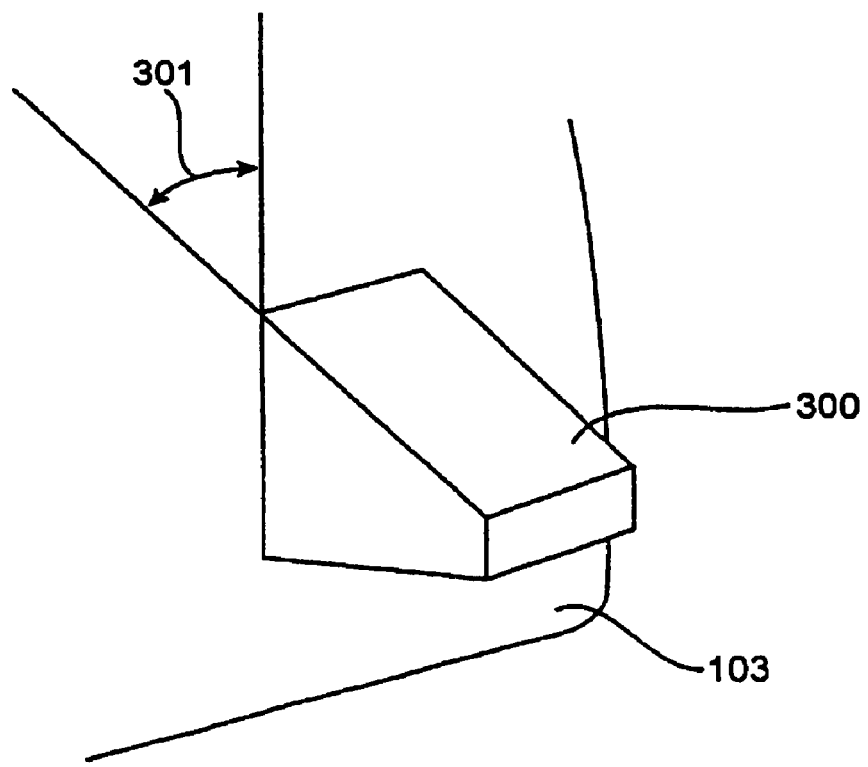
FIG. 8 is a detailed view of the attachment device of FIG. 7.
Figure 9A:
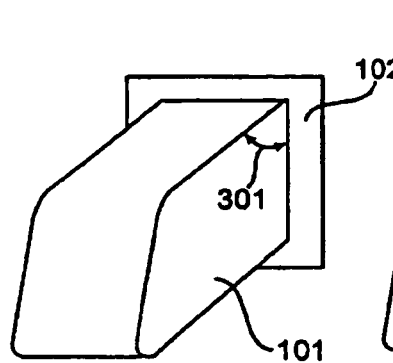
FIGS. 9A-9L are perspective views of a series of exemplary attachment devices with sloping angles constructed in accordance with the principles of the present invention.
Figure 9B:
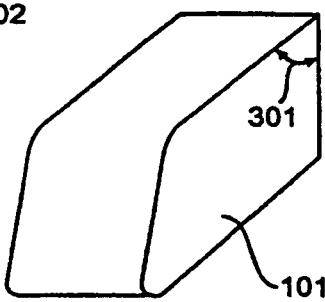
Figure 9C:
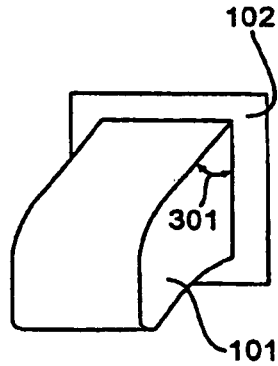
Figure 9D:
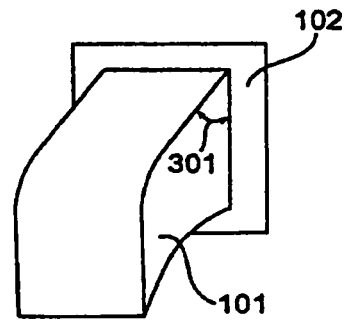
Figure 9E:
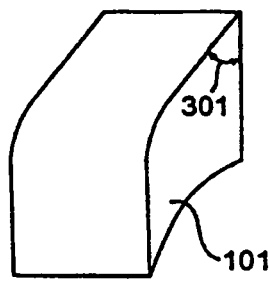
Figure 9F:
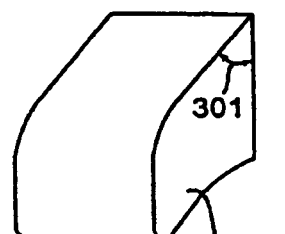
Figure 9G:
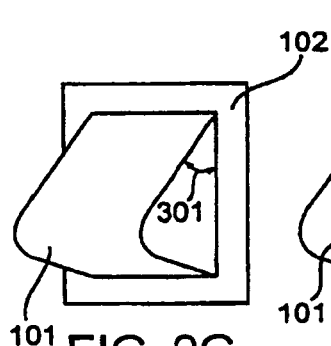
Figure 9H:
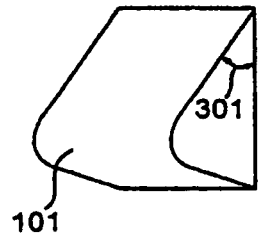
Figure 9I:
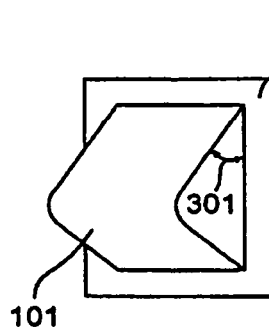
Figure 9J:
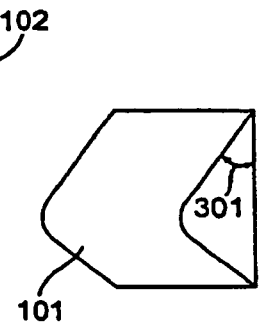
Figure 9K:
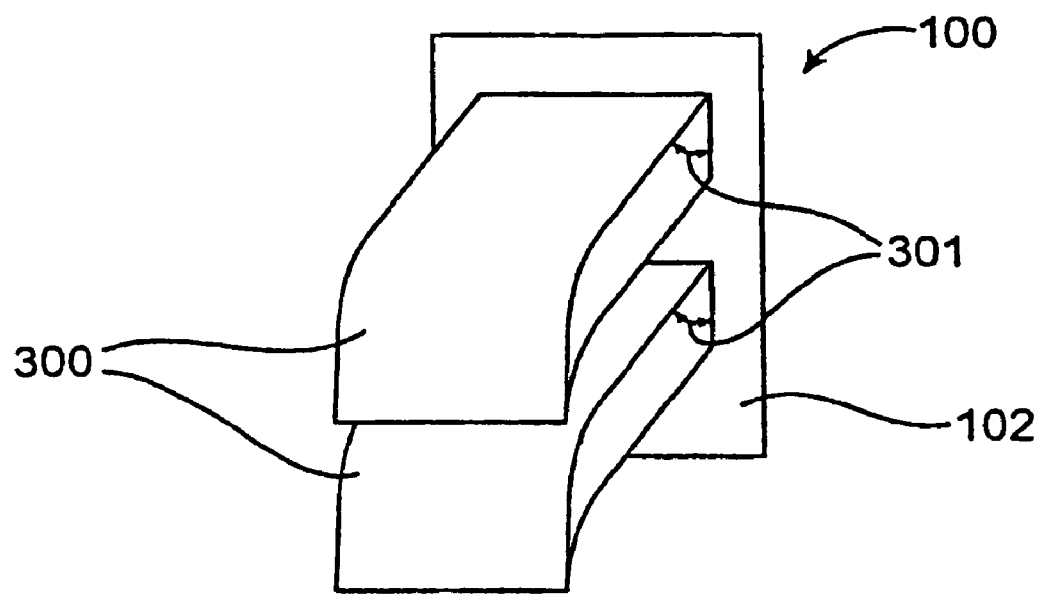
Figure 9L:
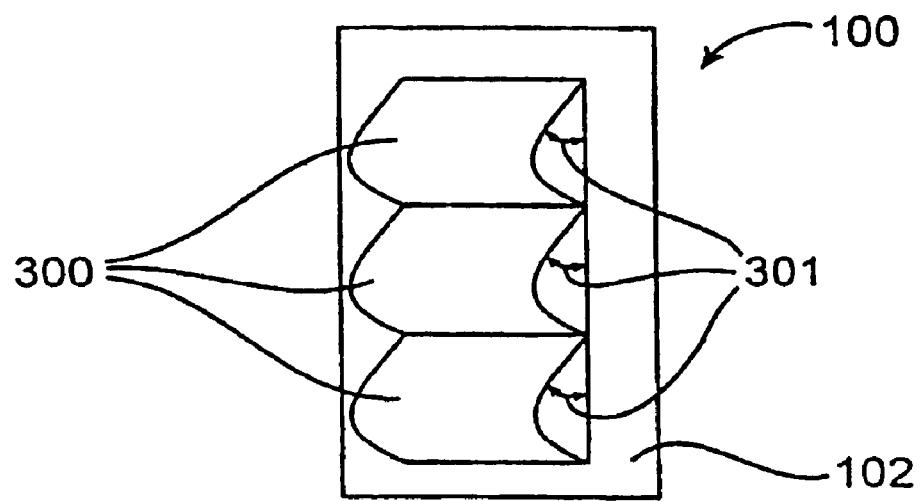
Figure 10A:
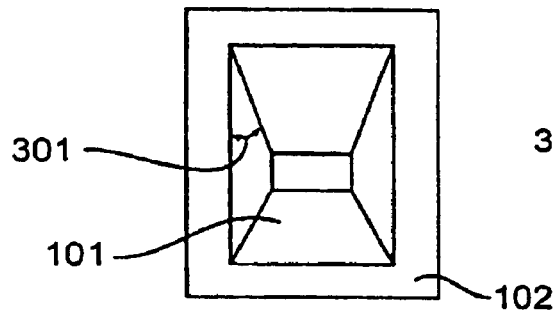
FIGS. 10A-10F are front views of a series of attachment devices having wedge-shaped structures with different front end geometries.
Figure 10B:
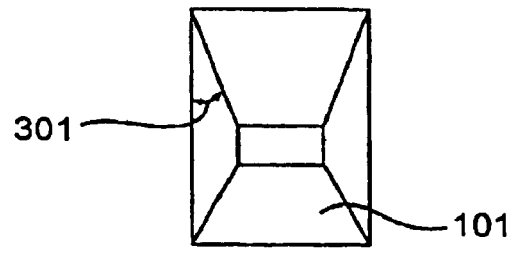
Figure 10C:
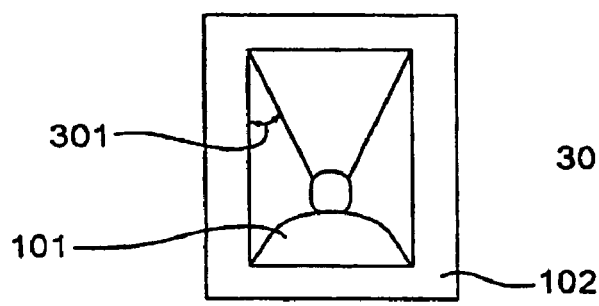
Figure 10D:
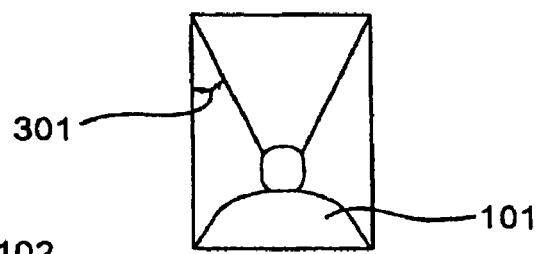
Figure 10E:
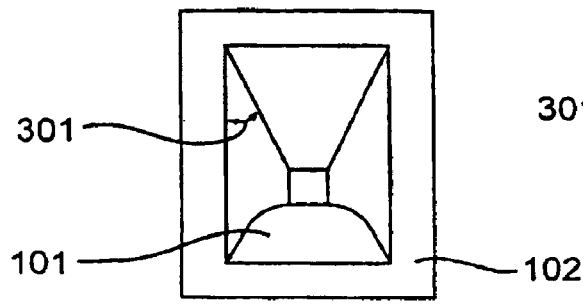
Figure 10F:
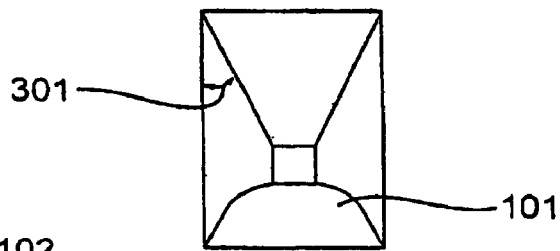

Referring now to FIG. 7, a preferred embodiment of an attachment body 101 design is illustrated for use in aiding the proper seating of a removable elastic repositioning appliance 105 and anchoring the appliance 105 in place to apply repositioning forces. Such attachment bodies 101 may be located on any surface of a dental feature and may be placed singly or in groups. The design of the attachment body 101 may include a structure 300 which protrudes perpendicularly from the surface of the tooth 103. As shown in FIG. 8, the structure 300 may contain a sloping angle 301, from the surface of the tooth 103 to the opposing end of the structure 300, which is preferably less than 90 degrees. FIG. 9A presents a perspective view of a variety of attachment bodies 101 having sloping angles 301 as described. FIG. 9B presents a perspective view of attachment bodies 101 having a series protruding structures 300 (FIG. 8) with sloping angles 301. These designs may provide a means for a type of ratcheting action that would allow an appliance to be seated or positioned at differing levels. It may be appreciated that such designs may serve the same function without sloping angles 301 and with differing geometries. Similarly, FIGS. 10A-10F presents a front view of a variety of attachment devices 100 having sloping angles 301.

Referring back to FIG. 7, when the elastic positioning appliance 105 is inserted for placement, the protruding structure 300 may grossly align with a matching negative impression 302 of the structure 300 formed into the appliance 105. As the appliance 105 is seated, the slope of the protruding structure 300 may guide the appliance 105 into the proper position. Once in position, the attachment body 101 may serve as an anchor for the appliance 105 to apply repositioning forces. Additionally, the elastic appliance 105 and/or the attachment body 101 may change in shape, stiffness or orientation to implement such anchoring. These changes may be the result of state changes of one or more layers of the material when subjected to a certain environmental condition, such as non-physiologic pH, temperature, ionic strength or external stimulus.

Repositioning forces as a result of anchoring may take many forms. In a preferred embodiment illustrated in FIG. 11, attachment devices 100 may be placed to serve as anchors to apply directed intrusive repositioning forces. As shown in Step 1, two attachment devices 100 may be placed on each of two teeth 103 located on opposites sides of one or a contiguous group of between teeth 103'. In Step 2, an elastic repositioning appliance 105 is produced with an inset profile 303 at the location in which intrusive force is to be applied. In Step 3, the appliance 105 is inserted for placement over the teeth 103,103'. In Step 4, the appliance 105 is attached to the attachment devices 100 which serve to anchor the appliance 105. As a result, intrusive forces, depicted by a downward arrow 304, are applied to the between teeth 103'. Over time, the intrusive forces will affect intrusion of the between teeth 103', as shown in Step 5. It may be appreciated that the profile of the appliance 105 may take a variety of forms to create intrusive forces, depending on the overall configuration of the teeth 103 and the between teeth 103'. For example, in the case where the between teeth 103' are initially more extruded than the adjacent teeth 103, the appliance 105 may have a profile that is generally flat, with no inset profile 303. Thus, when the appliance 105 is attached to the attachment devices 100, intrusive forces will again be applied to the between teeth 103'. The use of bonded devices, such as attachment devices, to apply repositioning forces to a tooth without bonded devices is distinct in that it is counterintuitive to the methods of conventional orthodontics in which brackets are bonded to the teeth that require repositioning.

Figure 12A:
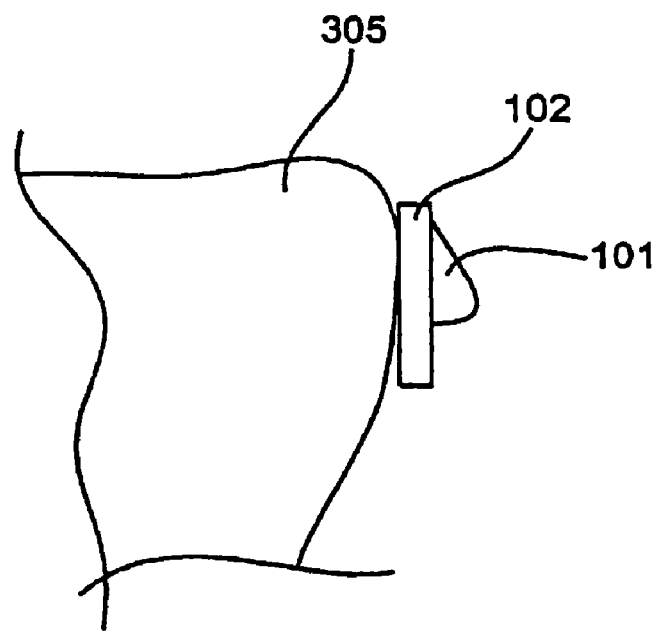
FIGS. 12A and 12B illustrate the mounting of an attachment device according to the present invention to a tooth surface.
Figure 12B:
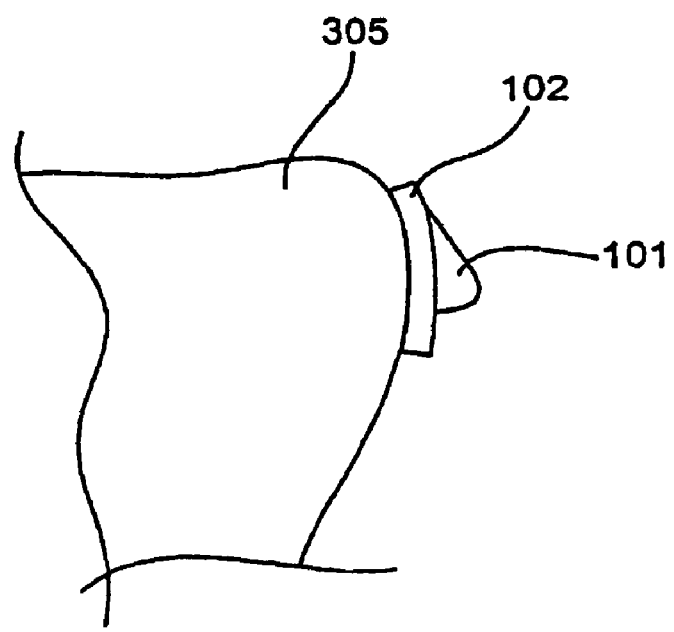

As previously described, the attachment devices may be constructed from a variety of materials, including materials which have been formulated to be sensitive to an environmental condition or external stimulus. For example, upon exposure, a rigid material may become temporarily malleable, allowing changes in geometry to be made. Upon removal of the condition or stimulus, the material may return to its original rigid state with the new geometry. This may be particularly useful in conforming the geometry of an attachment body 101 to better interface an uneven or curved surface. As shown in FIG. 12A, an attachment body 101 may be originally constructed to have an attachment base 102 which does not conform to the dental surface 305 to which it is to be bonded. In this case, the material may be exposed to a stimulus to which it is sensitive, initiating a state change in the material. Such a stimulus may be a change in the oral environment to a non-physiologic pH, temperature, ionic strength or liquid absorption. Likewise, the stimulus may be of an external source such as light, magnetism, electricity, radiowaves, or chemicals. Such a state change may allow the material to become flexible so the attachment base 102 may conform to the dental surface 305, as shown in FIG. 12B.

Similarly, a permanent state change in the material may occur as a result of applying a stimulus. Thus, the material may be malleable in its initial state, allowing it to be molded into a desired shape. The material may then be polymerized due to application of a stimulus. Likewise, polymerization may occur over time from the point of initial formulation, as in the case of an air or moisture cure. Polymerization may simultaneously harden the material and form a bond between the material and any interfacing surface.

A series of methods are provided based on these polymerization characteristics to produce and/or bond an attachment body 101 to a dental feature, such as a tooth. Three preferred embodiments are applicable for use with elastic positioning appliances and are as follows: 1) basic casting, 2) casting with polymerizing material and 3) computer-aided casting with polymerizing material.

Figure 13A:
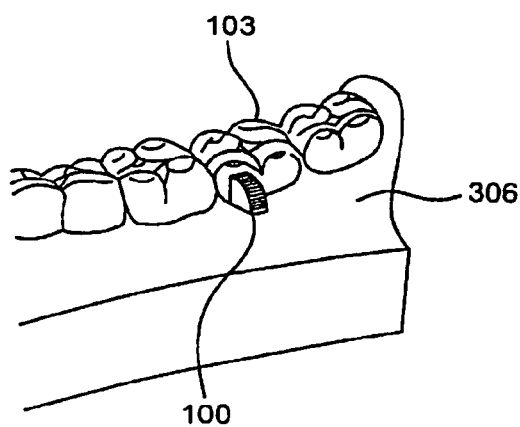
FIGS. 13A-13D illustrate an embodiment of the method of basic casting.
Figure 13B:
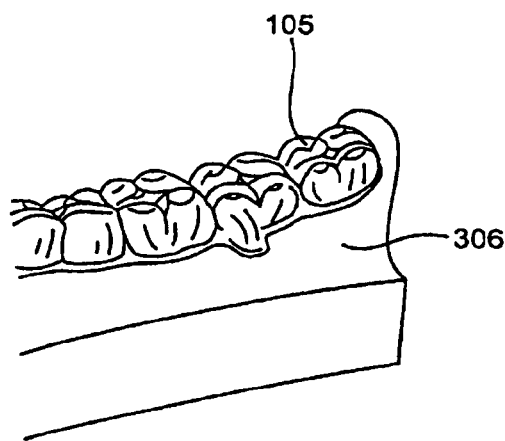
Figure 13C:
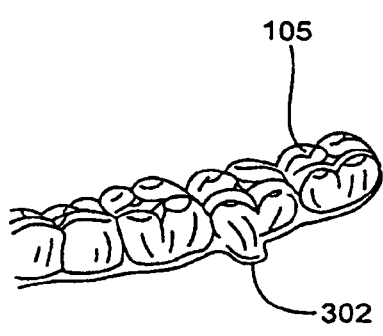
Figure 13D:
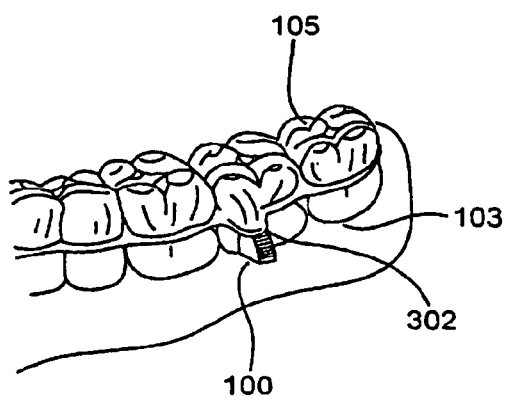

FIGS. 13A-D characterize an embodiment of the method of basic casting. Basic casting involves first producing two identical attachment devices 100 by any means. As shown in FIG. 13A, one attachment device 100 may be placed in a desired location on a mold 306 which replicates the dental feature of interest, in this case a tooth 103. As shown in FIG. 13B, an elastic positioning appliance 105 may be formed over a mold 306 containing the attachment device 100. This is typically accomplished by heating a thermoformable polymer material and applying vacuum or pressure to form the polymer to the mold. Alternatively, reaction casting may be used to produce such an appliance. Upon removal, FIG. 13C, a negative impression 302 of the attachment device may be seen in the wall of the appliance 105. The other attachment device 100 is placed in the identical location and orientation on the dental feature of the patient corresponding to the mold 306. When the appliance 105 is inserted and seated in position, the impression 302 in the appliance 105 will correspond with the attachment device 100 bonded to the tooth 103, as illustrated in FIG. 13D.

The method of casting with a polymerizing material is similar to the method of basic casting. In one embodiment, an elastic positioning appliance 105 is formed over a mold 306 containing an attachment device 100, as previously depicted in FIGS. 13A-C. At this point, a malleable polymerizing material 400 may be placed into the negative impression 302 in the appliance 105.

Figure 14A:
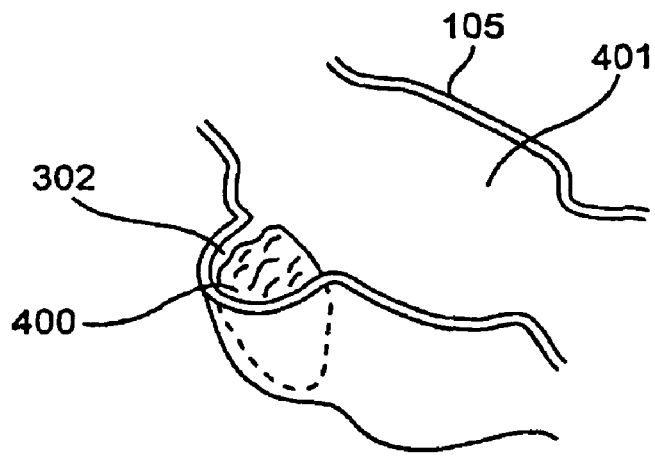
FIGS. 14A-14C illustrates features of the method of casting with a polymerizing material.
Figure 14B:
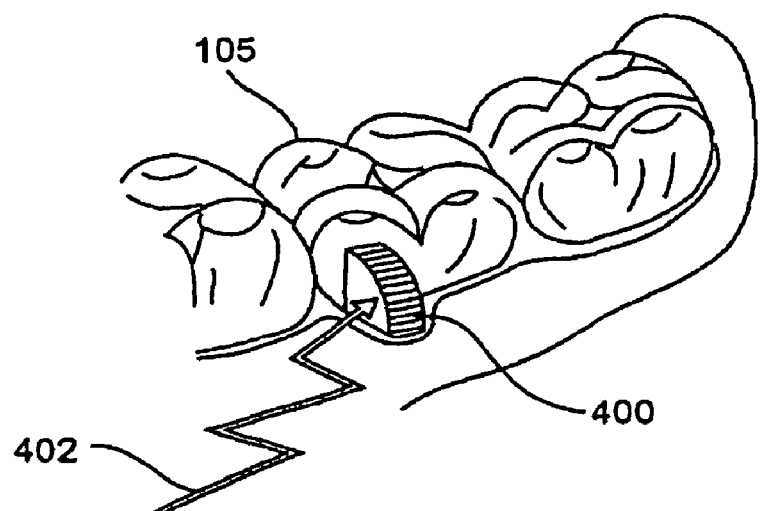
Figure 14C:
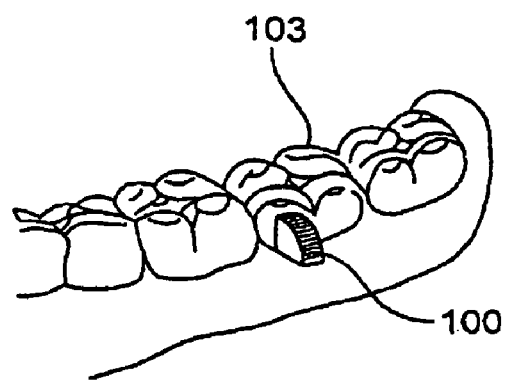

FIG. 14A is an enlarged view of the underside of a portion of the appliance 105, revealing a receiving cavity 401 for a tooth 103 and the negative impression 302 of an attachment device 100 filled with a polymerizing material 400. When the appliance 105 is seated in position in the oral cavity, FIG. 14B, the polymerizing material 400 will be in contact with the desired dental surface, in this case a tooth 103, and will be positioned in the proper location. The material 400 may be polymerized (depicted by jagged arrow 402) by any means, such as an external stimulus. Upon removal of the appliance 105, the formed attachment device 100 may remain in place on the tooth 103, as shown in FIG. 14C. Cross-sectional views of this method are presented in FIG. 14D.

Figure 15A:
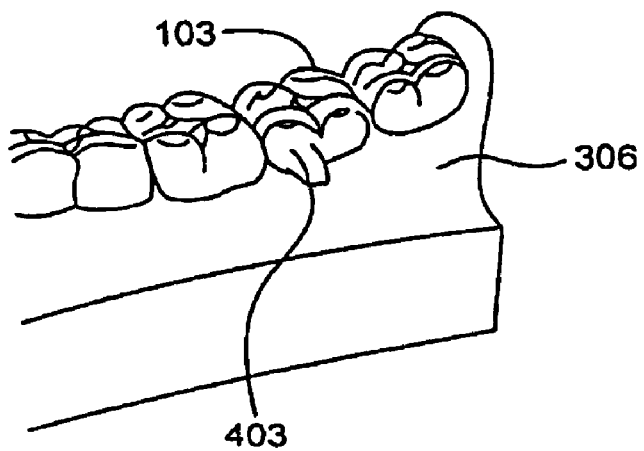
FIGS. 15A-15C illustrates features of the method of computer-aided casting with polymerizing material.
Figure 15B:
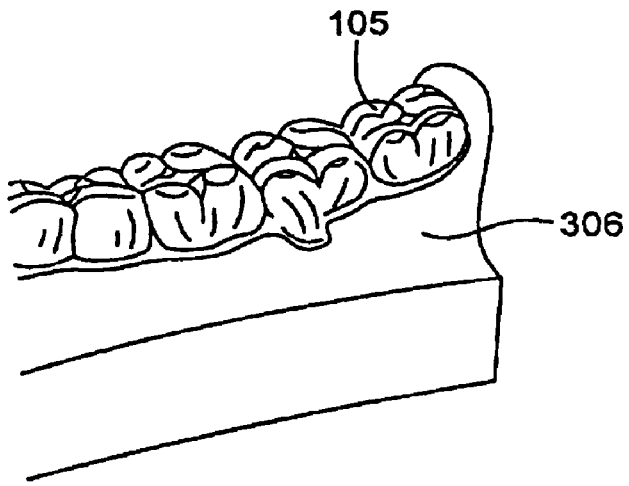
Figure 15C:
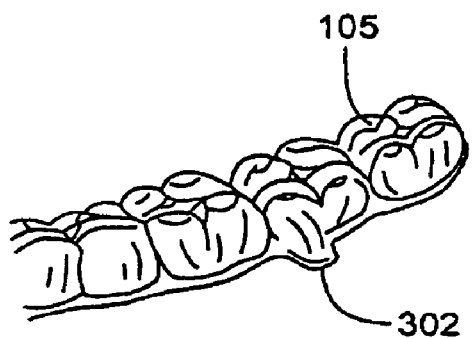

The method of computer-aided casting with polymerizing material 400 is similar to the methods described above, yet differs in the steps of creating the appliance 105. In one embodiment, a computerized image of the attachment device is virtually placed in a desired location on an image of the dental surface. From these images, a mold 306 is produced comprising the dental surface of interest, in this case a tooth 103, with an attachment device replica 403 in proper position. At this point, an elastic positioning appliance 105 may be formed over the mold 306, as seen in FIG. 15A. Upon removal, FIG. 15B, a negative impression 302 of the attachment device may be seen in the wall of the appliance 105. At this point, the attachment device 100 may be formed and bonded to the dental feature by methods previously depicted in FIGS. 14A-C.

Figure 16:
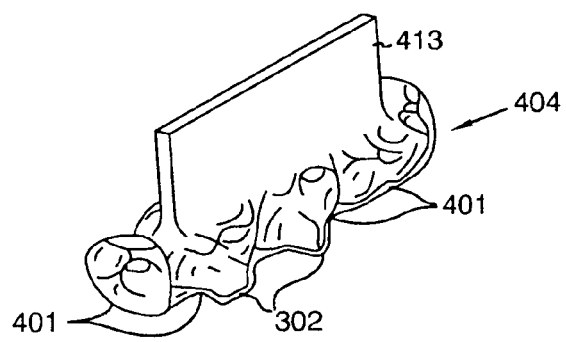
FIG. 16 illustrates an embodiment of a multi-tooth template having a handle for use in situ formation of attachment devices according to the methods of the present invention.

Two additional methods are provided to produce and/or bond an attachment device 100 to a dental feature, such as a tooth 103. These embodiments are applicable for use with any dental appliance. The first embodiment involves a multi-tooth template. The multi-tooth template may be similar or identical to an elastic repositioning appliance, and it may be used for casting with polymerizing material and computer-aided casting with polymerizing material, as described above. However, it may differ in that the template may not be used as the repositioning appliance. Therefore, multi-tooth template designs may include features that are not applicable to such use. For example, in FIG. 16, one embodiment depicts a type of handle 413 with which to easily place and remove the multi-tooth template 404. As shown, the template 404 may contain receiving cavities 401 for only a select portion of teeth and it may include negative impressions 302 for attachment devices on more than one tooth.

Figure 17A:
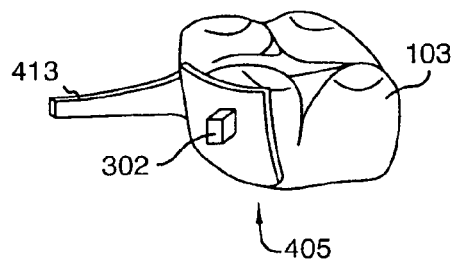
FIGS. 17A and 17B illustrate embodiments of single-tooth templates having handles for use in the methods of the present invention.
Figure 17B:
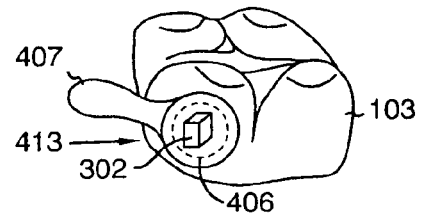

The second embodiment involves a single-tooth template. The single-tooth template is similar to the multi-tooth template 404, however it may be more rigid as it is designed to fit over a single dental feature. As shown in FIG. 17A, one embodiment may contain a portion of a receiving cavity which conforms to a portion of the surface of the target tooth 103. It may also contain a type of handle 413 to aid in placement of the single-tooth template 405. Production and bonding of an attachment device to the tooth 103 may be accomplished by casting with polymerizing material or computer-aided casting with polymerizing material. Similarly, an additional embodiment of a single-tooth template 405 may be seen in FIG. 17B. Here the template 405 may be thin and flexible to conform to a portion of a dental feature. It may contain adhesive ring 406 around the negative impression 302 of the attachment device. The adhesive ring 406 will hold the template 405 in place on the dental feature, in this case a tooth 103, throughout the casting with polymerizing material or computer-aided casting with polymerizing material to produce and bond the attachment device 100. A pull-tab 407 may be present to facilitate a peeling removal of the template 405.

Figure 18:
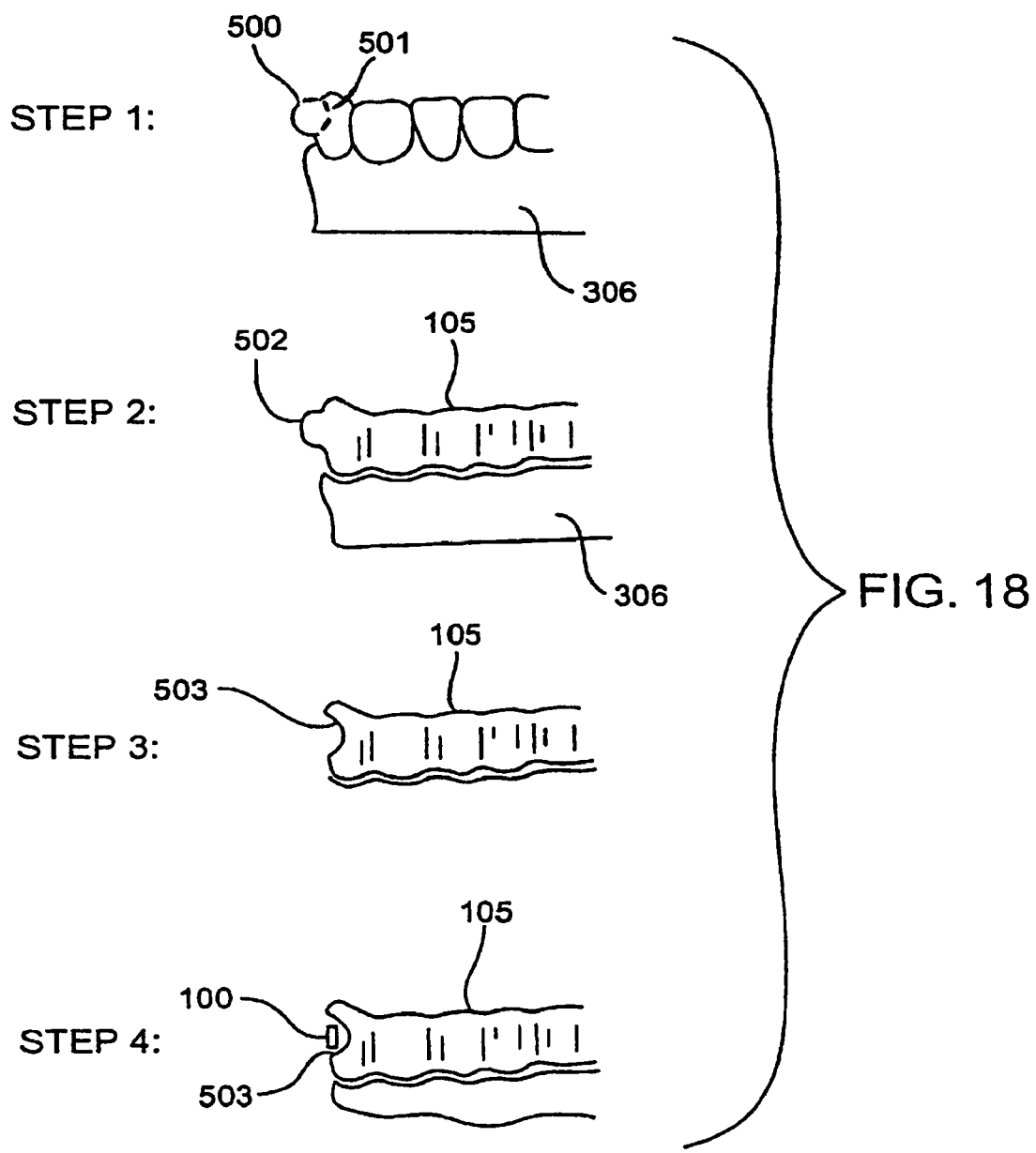
FIG. 18 illustrates a method according to the present invention for forming a window in a tooth positioning appliance using a feature formed in a mold according to the methods of the present invention.

A method to further aid in production of templates or elastic positioning appliances in depicted in FIG. 18. Here, an embodiment of an improved method for producing a window of particular shape and location in an elastic appliance is presented to prevent interference with specific devices or dental features. As shown in Step 1, a mold 306 is created with an added structure 500 in the location where the window is desired. The shape of the structure 500 should provide a cross-section (dashed line 501) that will form the shape of the window. In this example, the structure 500 is a sphere having a circular cross-section 501. In Step 2, a polymer sheet is thermoformed over the mold 306, and an elastic appliance 105 is produced with a spherical protrusion 502 in the location of the structure 500. After removal of the appliance 105 from the mold 306, the spherical protrusion 502 may be removed, as shown in Step 3, leaving a window 503 with the same shape as the cross-section 501 of the structure 500. In Step 4, the appliance 105 may be positioned on the dental features of the patient, allowing an attachment device 100 to be accessible through a window 503.

In one aspect, a polar attachment has two or more ends that have a fixed spatial or planar relationship between the buccal and lingual portions. The buccal and lingual portions need not have the same geometry. A specific positional relationship between buccal and lingual ends can be effected when the attachment is placed in the tooth. In this embodiment, a polar attachment is one body that passes through a target tooth to create both a buccal and lingual geometry at the same time with specific, set relative positions.

In another aspect, a polar attachment is one body that passes through a target tooth to create both an occlusal or incisal and either a buccal or a lingual geometry at the same time with specific, set relative positions.

In another aspect, a polar attachment is one body that passes through a target tooth to create both an occlusal and an incisal geometry at the same time with specific, set relative positions. In yet another aspect, systems and methods are disclosed for producing a digital model by providing a digital model of a tooth; providing a digital model of at least one attachment device having two or more portions, the digital model of the attachment device having the two or more portions extending through two or more surfaces of the tooth; and positioning the digital model of the attachment device on the digital model of the tooth to produce a combined computerized model.

Advantages of such attachments include greater accuracy and less operator training. Further, one attachment body is used in place of what now requires two separate bodies. The result is time savings on the operator in placing as well as aligning two separate bodies.

Figure 19A:
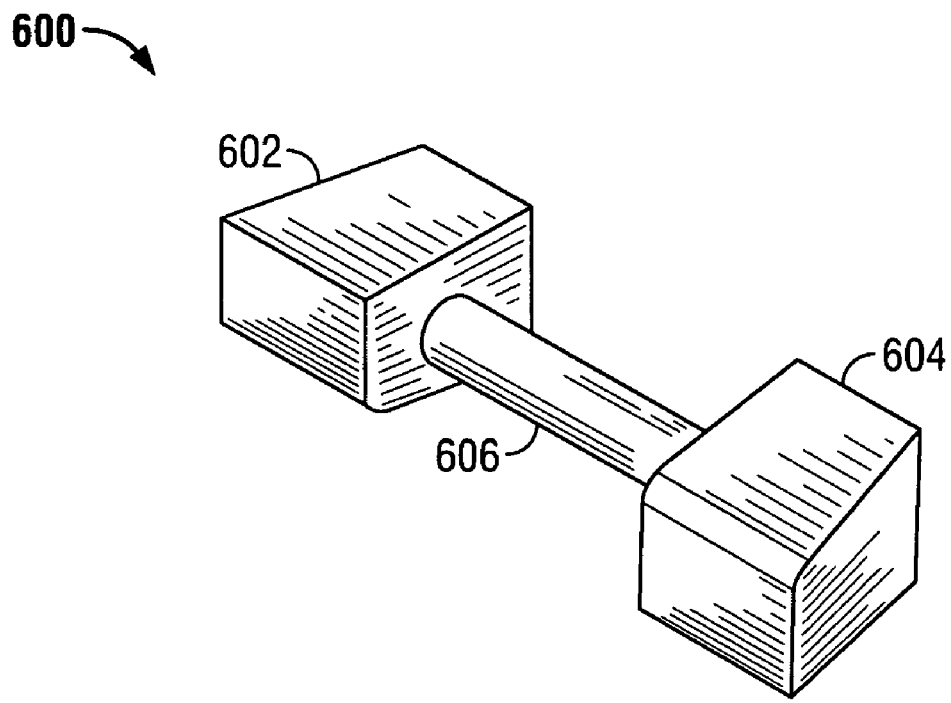
FIGS. 19A-19B show two views of exemplary polar attachment devices.
Figure 19B:
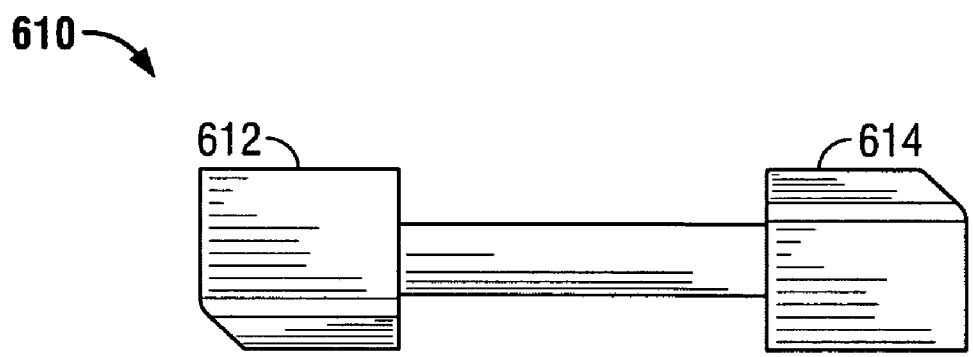

FIGS. 19A-19B show two views of exemplary polar attachment devices 600 and 610. The polar attachment devices 600 and 610 are digital models in one embodiment. During use, an operator and/or automatic placement software select(s) one of the attachment devices and manipulate(s) the selected attachment device to a desired position on a digital model of a tooth. A combined geometry of the combined digital model of the tooth and the selected attachment device is generated. The combined geometry can then be sent to a suitable rapid prototyping machine such as a stereolithography apparatus (SLA) to form a mold. The mold is then used to make a dental appliance or an attachment template as is known in the art.

In FIG. 19A, the polar attachment device has two ends or portions 602-604 that extend through lingual and buccal surfaces of a tooth. The shape of the ends or portions 602-604 can be any arbitrary three-dimensional shape. The ends 602-604 are connected by a bar 606. During the generation of the combined geometry, the bar 606 and inner sections of the portions 602-604 are subsumed in the geometry of the tooth model. Thus, only the tooth model and sections of the portions 602-604 that protrude from the tooth model remain.

FIG. 19A has ends that are symmetrically positioned. In FIG. 19B, an attachment device 610 has polar attachment ends 612-614 that are rotated relative to each other. Additionally, FIGS. 19A-19B have portions 602/604 and 612/614 that are positioned 180° apart from each other, other embodiments can have portions that are positioned 90° apart.

Figure 20:
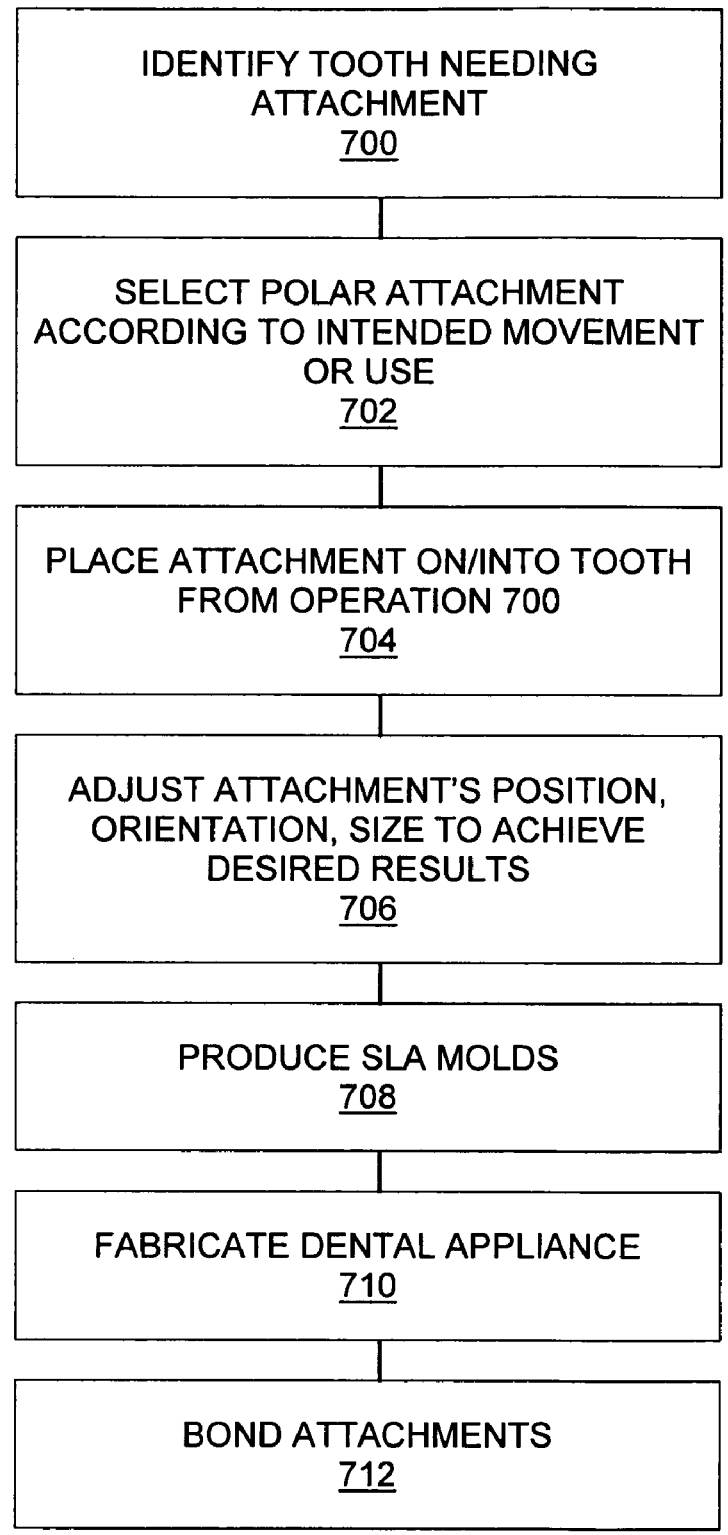
FIG. 20 shows an exemplary process for using the polar attachments of FIGS. 19A-19B.

FIG. 20 shows an exemplary process for using the polar attachments of FIGS. 19A-19B. An attachment device is an object bonded to a tooth surface to assist in the movement of that tooth with a dental appliance. In this process, an object starts as a computer representation of a specific geometry which is virtually placed on a tooth. The SLA production process renders it in its positive form on the arch or arches on which it appears. The fabrication process then forms the object's negative representation as a cavity for a dental appliance or for an attachment template.

In the case of an attachment template, the cavity in the attachment template is filled with a material, typically a dental composite. The attachment template is placed on the patient's teeth, and the fill material is cured. The curing hardens the fill material and bonds the fill material to the tooth. During treatment, the hardened material in the cavity cooperates with a removable dental appliance to assist in moving the underlying tooth.

In FIG. 20, a virtual model of a tooth that needs an attachment is identified (700). Next, a polar attachment computer model is selected (702). In one embodiment, a polar attachment with two or more ends that have a fixed spatial or planar relationship between the buccal and lingual portions can be selected. The buccal and lingual portions need not have the same geometry. In another embodiment, a polar attachment can be selected with one body that passes through a target tooth to create both an occlusal or incisal and either a buccal or a lingual geometry at the same time with specific, set relative positions.

The attachment is placed on the tooth model (704). A specific positional relationship between buccal and lingual ends is effected when the attachment is placed in the tooth. In one embodiment, the polar attachment body passes through a target tooth to create both a buccal and lingual geometry at the same time with specific, set relative positions.

The operator or placement software can adjust the attachment's position, orientation and size, among others, to achieve a desired result (706). For example, the buccal and lingual portions or the occlusal and incisal portions need not have the same geometry. The polar attachments provide for greater accuracy in positioning the attachments and less operator training. Further, one attachment body is used in place of what now requires two separate bodies. The result is time savings on the operator in placing as well as aligning two separate bodies.

Upon final placement, a digital model of the attachment device having the two or more portions extending through two or more surfaces of the tooth as positioned on the digital model of the tooth is combined with the digital model of the tooth. One exemplary combination is shown in FIGS. 21A, 21B and 21C.

The combined digital model is used to produce a mold using techniques known in the art such as stereo-lithography apparatus (SLA) or other suitable rapid prototyping technology (708). Next, a dental appliance template is fabricated (710), and the attachments can be formed on the tooth (712) using techniques discussed above.

Turning now to FIG. 21A, a side view of a digital tooth model with an embedded polar attachment is shown. A corresponding cross-sectional view of the tooth/embedded polar attachment is shown in FIG. 21B. While in the placement mode, the operator and/or automatic placement software can adjust the attachment's position, orientation and size, among others. FIG. 21C illustrates an exemplary combination of tooth and polar attachment. Such a combined digital model is then fabricated as a mold using SLA, for example.

The data processing aspects of the invention can be implemented in digital electronic circuitry, or in computer hardware, firmware, software, or in combinations of them. Data processing apparatus of the invention can be implemented in a computer program product tangibly embodied in a machine-readable storage device for execution by a programmable processor; and data processing method steps of the invention can be performed by a programmable processor executing a program of instructions to perform functions of the invention by operating on input data and generating output. The data processing aspects of the invention can be implemented advantageously in one or more computer programs that are executable on a programmable system including at least one programmable processor coupled to receive data and instructions from and to transmit data and instructions to a data storage system, at least one input device, and at least one output device. Each computer program can be implemented in a high-level procedural or object oriented programming language, or in assembly or machine language, if desired; and, in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented using a computer system having a display device such as a monitor or LCD (liquid crystal display) screen for displaying information to the user and input devices by which the user can provide input to the computer system such as a keyboard, a two-dimensional pointing device such as a mouse or a trackball, or a three-dimensional pointing device such as a data glove or a gyroscopic mouse. The computer system can be programmed to provide a graphical user interface through which computer programs interact with users. The computer system can be programmed to provide a virtual reality, three-dimensional display interface.

The invention has been described in terms of particular embodiments. Other embodiments are within the scope of the following claims. For example, the steps of the invention can be performed in a different order and still achieve desirable results.

What is claimed is:

1. A method for producing a dental positioning appliance which is removably attachable to at least one tooth to effect or enhance dental positioning, said method comprising:
   providing a digital model of an attachment device and a digital model of a tooth, the digital model of the attachment device having adjustable portions extending through at least two surfaces of the digital model of the tooth, wherein the at least two surfaces of the digital model of the tooth correspond to at least a buccal surface and a lingual surface of the at least one tooth;
   providing a mold produced based on the digital models of the attachment device and the tooth wherein the mold includes a molded tooth having an attachment device mounted or formed thereon, the attachment device on the mold having a fixed spatial or planar relationship between at least two surfaces of the molded tooth;
   forming the dental positioning appliance over the mold; and
   removing the dental positioning appliance from the mold, wherein the dental positioning appliance has:
      at least two receptacles corresponding to the attachment device on the mold, the at least two receptacles formed to receive the attachment device on the mold when the attachment device on the mold is attached to the molded tooth and;
      a tooth receiving cavity corresponding to the molded tooth.

2. A method as in claim 1, wherein the method further comprises:
   providing additional structures on the mold, wherein the appliance has protrusions corresponding to the structures; and
   removing the appliance from the mold utilizing the protrusions.

3. A method for producing a digital model, said method comprising:
   providing a digital model of at least one tooth that is to have at least one attachment device attached thereto;
   providing a digital model of the at least one attachment device, the digital model of the at least one attachment device having adjustable portions extending through at least two surfaces of the digital model of the at least one tooth, wherein the at least two surfaces of the digital model of the at least one tooth correspond to at least a buccal surface and a lingual surface of the at least one tooth; and
   positioning the digital model of the at least one attachment device on the digital model of the at least one tooth to produce a combined computerized model.

4. A method for producing a dental positioning appliance which is removably attachable to at least one tooth to effect or enhance dental positioning, said method comprising:

providing a combined digital model of at least one tooth that is to have at least one attachment device attached thereto, a digital model of at least one attachment device having at least two adjustable portions extending through at least two surfaces of the digital model of the at least one tooth, wherein the at least two surfaces of the digital model of the at least one tooth correspond to at least a buccal surface and a lingual surface of the at least one tooth;

producing a mold from the combined digital model, wherein the mold has the at least one attachment device on the at least two surfaces of at least one molded tooth, the attachment device having a fixed spatial or planar relationship between the at least two surfaces of the at least one molded tooth;

forming a dental positioning appliance over the mold; and removing the dental positioning appliance from the mold, wherein the dental positioning appliance has:
   at least two receptacles corresponding to the at least one attachment device of the mold, the at least two receptacles formed to receive the at least one attachment device when the at least one attachment device is attached to at least one tooth; and
   one or more cavities corresponding to the at least one molded tooth.

5. A method as in claim 4, wherein the method further comprises:
   providing a digital model of an additional structure; and
   positioning the digital model of the additional structure on the digital model of the at least one tooth, wherein the dental positioning appliance has protrusions corresponding to the structures.

6. A method as in claim 4, wherein the method further comprises:
   providing a digital model of an additional structure; and
   positioning the digital model of the additional structure on the digital model of the at least one tooth.

7. A method for moving teeth, said method comprising:
   providing a digital model of at least one attachment device and a tooth, the digital model of the at least one attachment device having adjustable portions extending through at least two surfaces of the digital model of the tooth, wherein the at least two surfaces of the digital model of the tooth correspond to at least a buccal surface and a lingual surface of the tooth;
   curing material to form at least one attachment device on a tooth, the at least one attachment device having a fixed spatial or planar relationship between a buccal portion and a lingual portion of the tooth as determined by the digital model;
   removably positioning a first dental positioning appliance over the tooth wherein the appliance comprises an elastic polymeric shell having a cavity which receives the tooth and two or more receptacles which receive the at least one attachment device; and
   removably positioning at least a second dental positioning appliance over the tooth, wherein the second dental positioning appliance comprises an elastomeric shell having a cavity which receives the tooth and two or more receptacles which receive the at least one attachment device, wherein at least one of the two or more receptacles and the cavity has a different configuration than that of the first dental positioning appliance.

8. A method as in claim 7, wherein the first and second dental positioning appliances apply repositioning force to the at least one attachment device.

9. A method as in claim 8, wherein the first and second dental positioning appliances are anchored with the at least one attachment device and apply a repositioning force to another tooth.

10. A method as in claim 7, wherein the first and second dental positioning appliances apply an extrusive force to the at least one attachment device.

11. A method as in claim 7, wherein the first and second dental positioning appliances apply a rotational force to the at least one attachment device.

12. A method as in claim 7, wherein the buccal and lingual portions do not have the same geometry.

13. A method for producing a digital model, said method comprising:
   providing a digital model of a tooth that is to have at least one attachment device attached thereto;
   providing a digital model of the at least one attachment device, the digital model of the at least one attachment device having two or more adjustable portions extending through two or more surfaces of the digital model of the tooth, wherein the two or more surfaces of the digital model of the tooth correspond to at least a buccal surface and a lingual surface of the tooth; and
   positioning the digital model of the at least one attachment device on the digital model of the tooth to produce a combined computerized model.

14. A method as in claim 13, further comprising adjusting at least one of the two or more adjustable portions of the digital model of the at least one attachment device's position, orientation, and size.

* * * * *